US010688007B2

(12) United States Patent
Wyatt et al.

(10) Patent No.: US 10,688,007 B2
(45) Date of Patent: Jun. 23, 2020

(54) COMPRESSION DEVICE

(71) Applicant: Recovery Force, LLC, Fishers, IN (US)

(72) Inventors: Matthew W. Wyatt, Fishers, IN (US); Brian J. Stasey, Fishers, IN (US); Mark Gummin, Silverton, OR (US)

(73) Assignee: Recovery Force, LLC, Fishers, IN (US)

( * ) Notice: Subject to any disclaimer, the term of this patent is extended or adjusted under 35 U.S.C. 154(b) by 590 days.

(21) Appl. No.: 15/479,347

(22) Filed: Apr. 5, 2017

(65) Prior Publication Data

US 2017/0252252 A1 Sep. 7, 2017

Related U.S. Application Data

(63) Continuation-in-part of application No. 15/206,498, filed on Jul. 11, 2016, which is a continuation-in-part
(Continued)

(51) Int. Cl.
*A61H 1/00* (2006.01)
*A61H 11/00* (2006.01)
(Continued)

(52) U.S. Cl.
CPC .............. *A61H 1/008* (2013.01); *A61H 7/001* (2013.01); *A61H 7/007* (2013.01); *A61H 11/00* (2013.01);
(Continued)

(58) Field of Classification Search
CPC .............. A61H 11/00; A61H 2011/005; A61H 2201/165; A61H 2201/0192; A61H 2209/20; A61F 5/02
See application file for complete search history.

(56) References Cited

U.S. PATENT DOCUMENTS 3,387,305 A * 6/1968 Shafer ................... A61F 5/0125
2/22
3,935,984 A * 2/1976 Lichowsky ............ A61B 5/022
600/499
(Continued)

FOREIGN PATENT DOCUMENTS

DE 19833801 A1 2/2000
GB 2504984 A 2/2014
(Continued)

OTHER PUBLICATIONS

European Search Report corresponding to International application No. PCT/US2016/041706, dated Jul. 30, 2019 (14 pages).

*Primary Examiner* — Justine R Yu
*Assistant Examiner* — Christopher E Miller
(74) *Attorney, Agent, or Firm* — Maginot, Moore & Beck, LLP

(57) ABSTRACT

A wearable massage and/or compression device for applying controllable scrolling or intermittent sequential forces, such as compression forces, to the body and limbs of a user comprises one or more shape-memory wires integrated into an article of clothing and configured to apply a compression pressure to the limb through the fabric body upon changing shape in response to a stimulus, a pre-tensioning apparatus in the form of a bungee cord associated with each shape memory wire, and a micro-processor based controller for selectively actuating the one or more shape memory wire to reduce the length of the shape memory wire to thereby apply pressure to the wearer's body.

18 Claims, 30 Drawing Sheets

Related U.S. Application Data of application No. 14/823,040, filed on Aug. 11, 2015, now Pat. No. 10,441,491, which is a continuation-in-part of application No. 14/485,690, filed on Sep. 13, 2014, which is a continuation-in-part of application No. 14/027,183, filed on Sep. 14, 2013, now Pat. No. 9,326,911.

(60) Provisional application No. 61/701,329, filed on Sep. 14, 2012.

(51) Int. Cl.
| | | |
|---|---|---|
| *A61H 7/00* | (2006.01) | |
| *G08C 17/02* | (2006.01) | |
| *A61N 1/04* | (2006.01) | |
| *A63B 69/36* | (2006.01) | |
| *A63B 69/10* | (2006.01) | |
| *A63B 69/00* | (2006.01) | |
| *G09B 19/00* | (2006.01) | |

(52) U.S. Cl.
CPC ........ *G08C 17/02* (2013.01); *A61H 2011/005* (2013.01); *A61H 2201/0103* (2013.01); *A61H 2201/0192* (2013.01); *A61H 2201/0207* (2013.01); *A61H 2201/0214* (2013.01); *A61H 2201/0228* (2013.01); *A61H 2201/0257* (2013.01); *A61H 2201/10* (2013.01); *A61H 2201/1207* (2013.01); *A61H 2201/164* (2013.01); *A61H 2201/165* (2013.01); *A61H 2201/169* (2013.01); *A61H 2201/1635* (2013.01); *A61H 2201/1697* (2013.01); *A61H 2201/501* (2013.01); *A61H 2201/5012* (2013.01); *A61H 2201/5015* (2013.01); *A61H 2201/5071* (2013.01); *A61H 2201/5082* (2013.01); *A61H 2201/5097* (2013.01); *A61H 2203/0425* (2013.01); *A61H 2203/0468* (2013.01); *A61H 2205/062* (2013.01); *A61H 2205/065* (2013.01); *A61H 2205/081* (2013.01); *A61H 2205/084* (2013.01); *A61H 2205/106* (2013.01); *A61H 2205/108* (2013.01); *A61H 2205/12* (2013.01); *A61H 2209/00* (2013.01); *A61H 2230/06* (2013.01); *A61H 2230/50* (2013.01); *A61N 1/0456* (2013.01); *A63B 69/002* (2013.01); *A63B 69/0059* (2013.01); *A63B 69/0071* (2013.01); *A63B 69/10* (2013.01); *A63B 69/36* (2013.01); *A63B 2209/10* (2013.01); *A63B 2213/004* (2013.01); *A63B 2220/56* (2013.01); *A63B 2220/64* (2013.01); *A63B 2225/50* (2013.01); *A63B 2225/62* (2013.01); *A63B 2225/64* (2013.01); *A63B 2230/06* (2013.01); *A63B 2230/50* (2013.01); *G09B 19/0038* (2013.01)

(56) References Cited

U.S. PATENT DOCUMENTS

| | | | | |
|---|---|---|---|---|
| 4,206,765 A * | 6/1980 | Huber | ............... | A61B 5/02141 600/490 |
| 4,574,789 A * | 3/1986 | Forster | ............... | A61H 1/0218 248/321 |
| 4,862,878 A | 9/1989 | Davison et al. | | |
| 5,261,871 A * | 11/1993 | Greenfield | ............ | A61F 5/0109 602/19 |
| 5,346,461 A * | 9/1994 | Heinz | ................... | A61F 5/028 128/121.1 |
| 5,683,353 A * | 11/1997 | Hamersly | ............ | A61F 5/0125 601/33 |
| 5,997,465 A * | 12/1999 | Savage | ............... | A62B 17/008 600/20 |
| 6,032,387 A | 3/2000 | Johnson | | |
| 6,338,723 B1 * | 1/2002 | Carpenter | ............ | A61F 13/069 602/60 |
| 6,537,237 B1 * | 3/2003 | Hopkins | ............... | A61F 5/0125 602/16 |
| 7,056,297 B2 * | 6/2006 | Dohno | ............ | A63B 21/00181 310/316.01 |
| 7,868,221 B2 * | 1/2011 | Munch-Fals | ........... | A61H 23/02 602/41 |
| 7,905,849 B2 * | 3/2011 | Park | ...................... | A61F 5/028 128/869 |
| 8,382,693 B1 * | 2/2013 | Guldalian | ............... | A61F 5/028 602/19 |
| 9,050,202 B2 * | 6/2015 | Bache | ........................ | A61F 2/80 |
| 9,161,878 B1 * | 10/2015 | Pamplin | ................. | A61H 23/02 |
| 9,872,790 B2 * | 1/2018 | Capra | ....................... | A61F 5/01 |
| 10,076,462 B2 * | 9/2018 | Johnson | ................ | A41D 1/005 |
| 2002/0052568 A1 * | 5/2002 | Houser | ................... | A42B 3/00 602/26 |
| 2002/0095750 A1 * | 7/2002 | Hammerslag | ........... | A43B 5/16 24/68 SK |
| 2002/0100188 A1 * | 8/2002 | Jacques | ................ | A43B 3/0005 36/50.1 |
| 2003/0144620 A1 * | 7/2003 | Sieller | .................... | A61F 5/0125 602/5 |
| 2003/0212356 A1 * | 11/2003 | Scorvo | ................. | A61F 5/0125 602/20 |
| 2005/0043657 A1 * | 2/2005 | Couvillon, Jr. | ........ | A61H 23/00 601/134 |
| 2005/0080367 A1 * | 4/2005 | March | .................. | A61H 9/0078 601/148 |
| 2005/0113729 A1 * | 5/2005 | Scott | .................... | A61F 13/085 602/19 |
| 2005/0273025 A1 * | 12/2005 | Houser | ................. | A61F 5/0123 602/16 |
| 2006/0083623 A1 * | 4/2006 | Higgins | ............... | A61H 9/0078 417/44.2 |
| 2006/0122544 A1 * | 6/2006 | Ciluffo | .............. | A41D 13/0015 601/15 |
| 2006/0156517 A1 * | 7/2006 | Hammerslag | ............ | A43B 5/16 24/68 SK |
| 2006/0287621 A1 * | 12/2006 | Atkinson | ............. | A61H 9/0078 601/151 |
| 2008/0060167 A1 * | 3/2008 | Hammerslag | ............ | A43B 5/16 24/68 SK |
| 2008/0066272 A1 * | 3/2008 | Hammerslag | .......... | A43C 11/16 2/455 |
| 2008/0195018 A1 * | 8/2008 | Larson | ............... | A61B 17/1325 602/53 |
| 2008/0255494 A1 * | 10/2008 | Rousso | ................... | A61F 13/06 602/62 |
| 2008/0262399 A1 * | 10/2008 | Kovelman | ........... | A61H 9/0078 601/152 |
| 2008/0319359 A1 * | 12/2008 | Moomiaie-Qajar | ... | A61H 11/00 601/152 |
| 2009/0024062 A1 * | 1/2009 | Einarsson | .......... | A41D 13/1281 600/595 |
| 2009/0082707 A1 * | 3/2009 | Rumsey | .................. | A61F 5/028 602/19 |
| 2009/0299242 A1 * | 12/2009 | Hasegawa | ............... | A61F 5/055 602/18 |
| 2010/0050478 A1 * | 3/2010 | DiBenedetto | ........ | A43B 1/0036 36/132 |
| 2010/0056966 A1 * | 3/2010 | Toth | .................... | A61H 23/0254 601/134 |
| 2010/0056973 A1 * | 3/2010 | Farrow | ................. | A61F 13/041 602/63 |
| 2010/0139057 A1 * | 6/2010 | Soderberg | ............. | A43C 11/16 24/68 R |
| 2010/0204803 A1 * | 8/2010 | Tozzi | .................... | A61F 2/0036 623/23.72 |
| 2010/0217167 A1 * | 8/2010 | Ingimundarson | ....... | A61F 5/028 602/19 |

(56) References Cited

U.S. PATENT DOCUMENTS

| | | | | |
|---|---|---|---|---|
| 2010/0274364 A1* | 10/2010 | Pacanowsky | ............. | A61F 2/60 623/36 |
| 2011/0066093 A1* | 3/2011 | Vess | ................. | A61H 11/00 601/148 |
| 2011/0178448 A1* | 7/2011 | Einarsson | ............ | A61F 5/0102 602/16 |
| 2012/0004587 A1* | 1/2012 | Nickel | ................. | A61F 5/0118 602/21 |
| 2012/0010547 A1* | 1/2012 | Hinds | ................... | A61F 5/0118 602/21 |
| 2012/0029404 A1* | 2/2012 | Weaver, II | ............ | A61F 5/0111 602/27 |
| 2012/0065561 A1* | 3/2012 | Ballas | ................. | A61H 9/0021 601/152 |
| 2012/0232447 A1* | 9/2012 | Gordon | ............... | A61H 9/0092 601/151 |
| 2012/0253252 A1* | 10/2012 | Weaver, II | ............ | A61F 5/0118 602/20 |
| 2013/0104429 A1* | 5/2013 | Torres | ................. | A43B 3/0005 36/136 |
| 2013/0138029 A1* | 5/2013 | Gerber | .................... | A43B 3/16 602/27 |
| 2013/0174859 A1* | 7/2013 | Bhat | ........................ | A61F 5/00 128/889 |
| 2013/0237891 A1* | 9/2013 | Fryman | .................... | A61F 5/02 602/19 |
| 2013/0289461 A1 | 10/2013 | Cropper et al. | | |
| 2013/0345612 A1* | 12/2013 | Bannister | .............. | A61B 5/1116 602/19 |
| 2014/0070042 A1* | 3/2014 | Beers | ...................... | A61F 5/028 242/413 |
| 2014/0082963 A1* | 3/2014 | Beers | ..................... | A43C 11/00 36/83 |
| 2014/0257156 A1* | 9/2014 | Capra | .................. | A61F 5/0102 602/5 |
| 2014/0303534 A1* | 10/2014 | Huffa | .................... | A61F 5/0109 602/6 |
| 2014/0303536 A1* | 10/2014 | Guldalian | ............... | A61F 5/028 602/19 |
| 2015/0059206 A1* | 3/2015 | Lovett | .................. | A43C 11/165 36/50.1 |
| 2015/0065930 A1 | 3/2015 | Wyatt et al. | | |
| 2015/0073318 A1* | 3/2015 | Holschuh | ................. | B64G 6/00 601/84 |
| 2015/0089839 A1 | 4/2015 | James et al. | | |
| 2015/0150705 A1* | 6/2015 | Capra | ....................... | A61F 5/01 602/6 |
| 2015/0190262 A1* | 7/2015 | Capra | .................. | A61F 5/0123 602/26 |
| 2016/0166463 A1* | 6/2016 | Douglas | ............... | A61H 9/0078 601/150 |
| 2016/0310310 A1* | 10/2016 | White | ....................... | A61F 5/02 |
| 2016/0331620 A1* | 11/2016 | Kazanchyan | .......... | A61H 1/006 |
| 2017/0027735 A1* | 2/2017 | Walsh | ................... | A61F 5/0102 |
| 2017/0143574 A1* | 5/2017 | Choi | ..................... | A61H 1/0244 |
| 2017/0304136 A1* | 10/2017 | Holschuh | .............. | A61H 1/008 |
| 2017/0354206 A1* | 12/2017 | Hammerslag | ............. | A43B 5/16 |
| 2018/0049903 A1* | 2/2018 | Witherspoon | ........... | A61H 1/02 |

FOREIGN PATENT DOCUMENTS

| | | |
|---|---|---|
| WO | 94/09728 | 5/1994 |
| WO | 02/054900 A1 | 7/2002 |
| WO | 2013/191933 A2 | 12/2013 |

\* cited by examiner

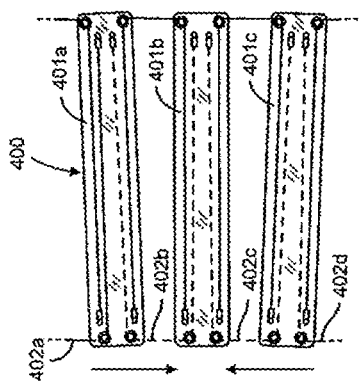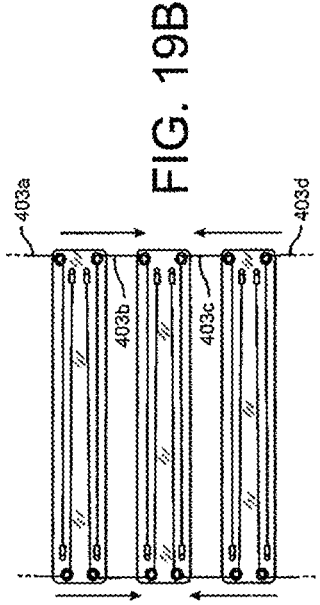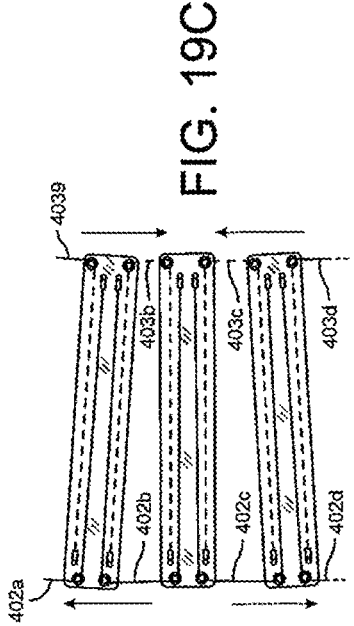
FIG. 19A
FIG. 19B
FIG. 19C
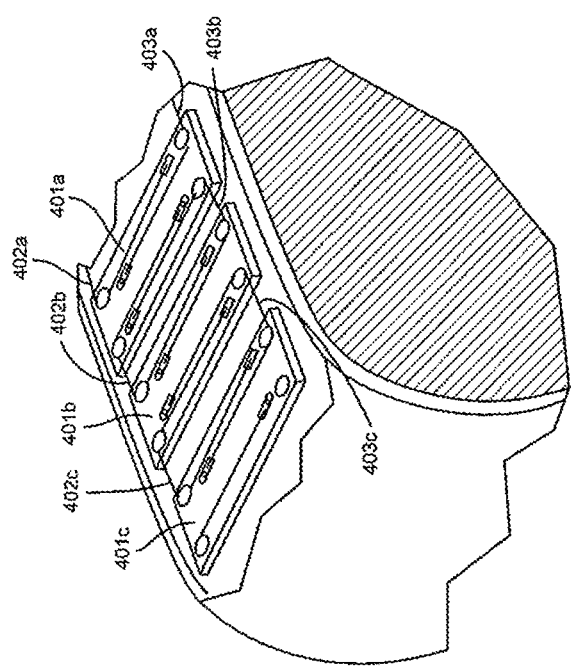
FIG. 18B

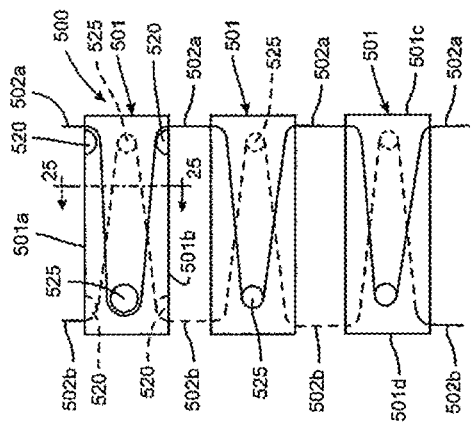
FIG. 24
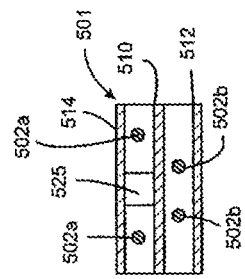
FIG. 25
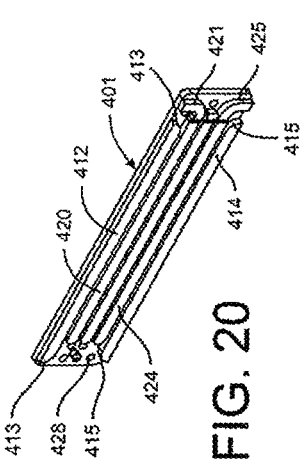
FIG. 20
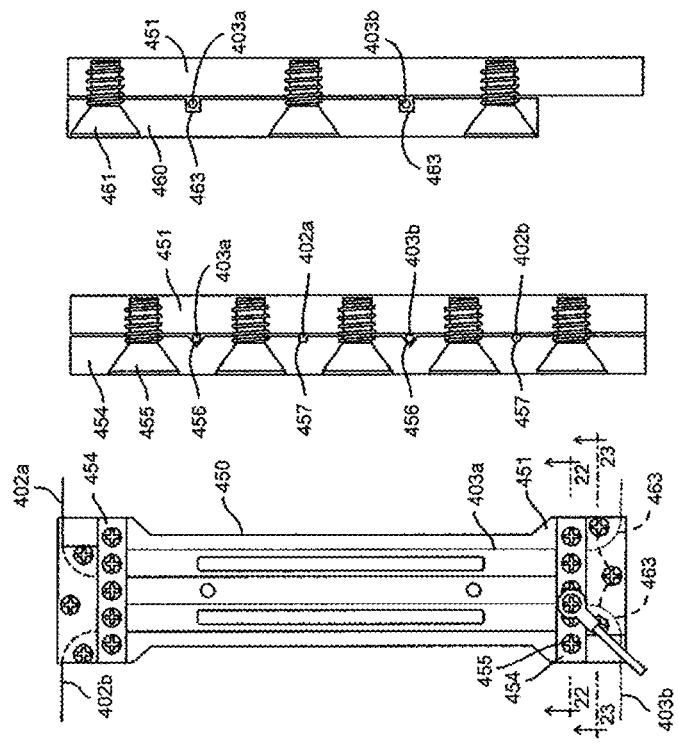
FIG. 22    FIG. 23
FIG. 21

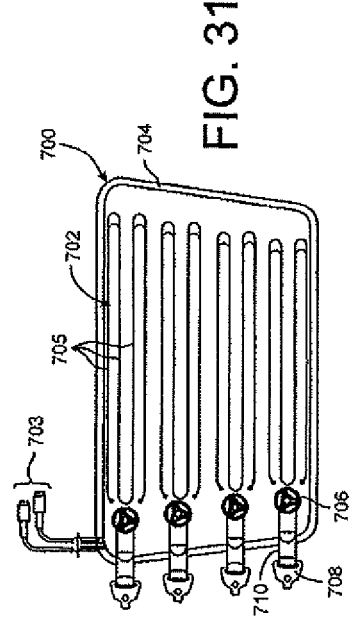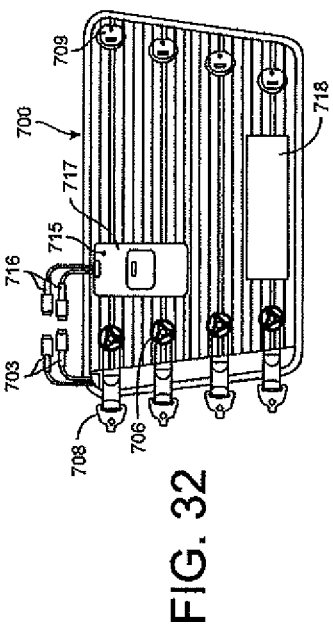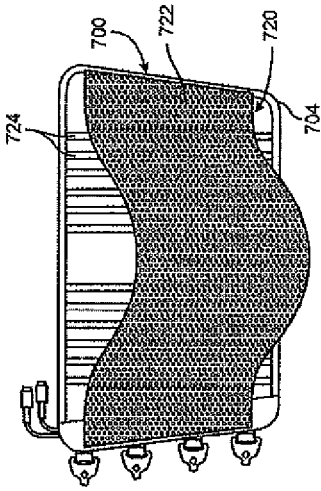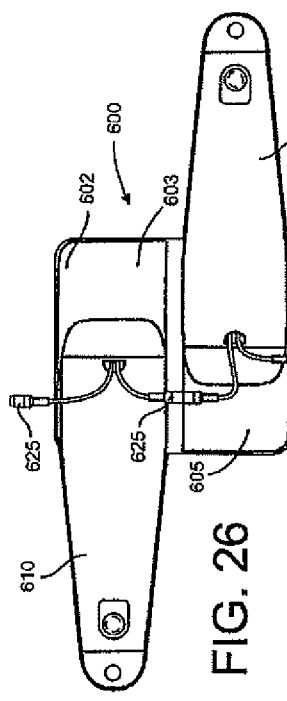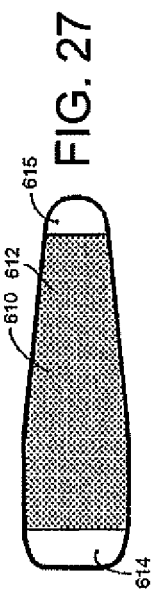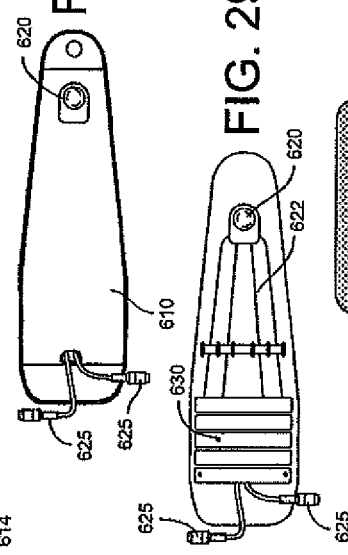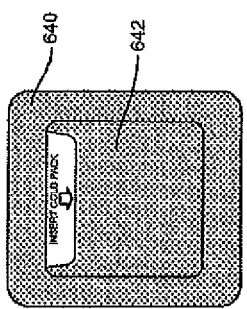

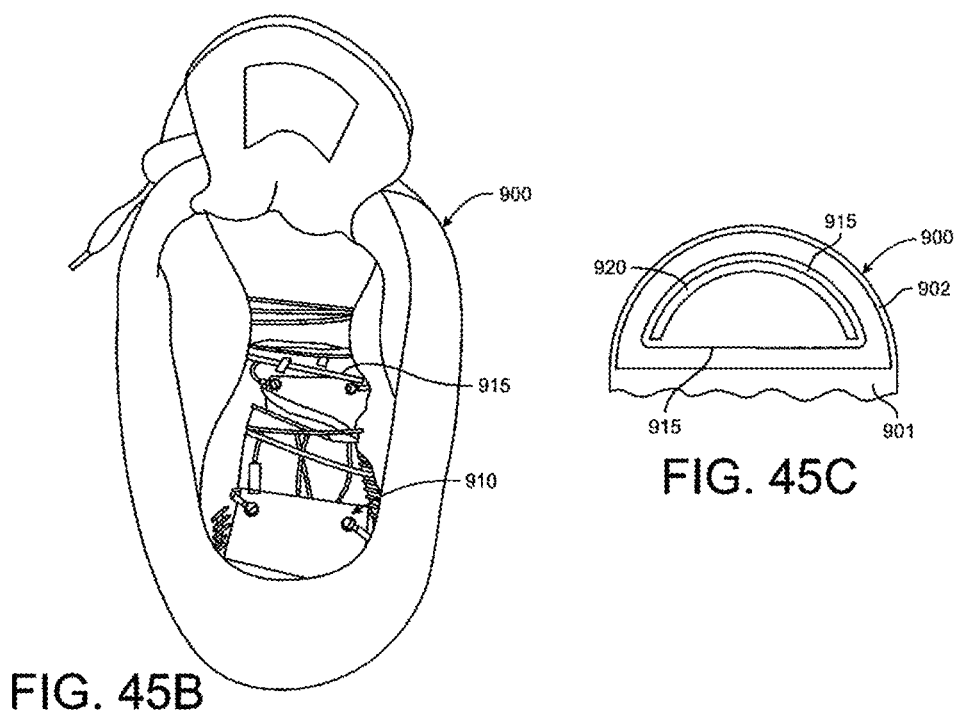
FIG. 45B
FIG. 45C
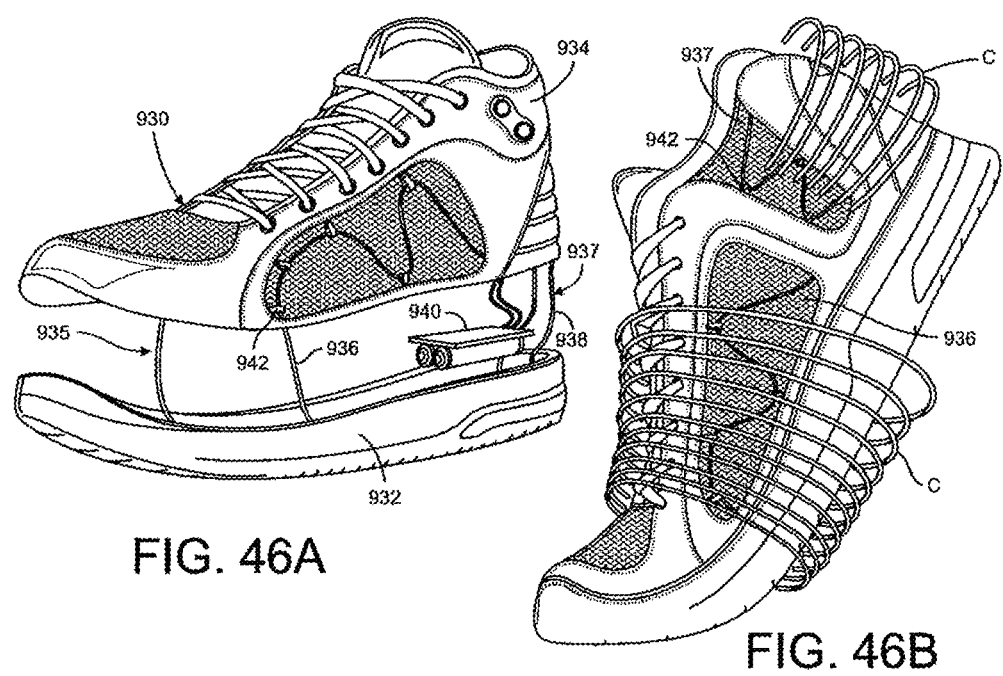
FIG. 46A
FIG. 46B

COMPRESSION DEVICE

CROSS-REFERENCE TO RELATED APPLICATION

This application is a continuation-in-part of and claims priority to co-pending U.S. application Ser. No. 15/206,498, filed on Jul. 11, 2016, which is a continuation-in-part of and claims priority to co-pending U.S. application Ser. No. 14/823,040, filed on Aug. 11, 2015, which is a continuation-in-part of and claims priority to co-pending U.S. application Ser. No. 14/485,690, filed on Sep. 13, 2014, which is a continuation-in-part of and claims priority to U.S. Pat. No. 9,326,911, which issued on May 3, 2016 and which is a utility conversion of and claims priority to provisional application Ser. No. 61/701,329, entitled "Automated Constriction Device, filed on Sep. 14, 2012, the entire disclosures of which are incorporated herein by reference.

BACKGROUND

Blood flow disorders can lead to numerous health and cosmetic problems for people. Relatively immobile patients, such as post-operative patients, the bedridden, and those individuals suffering from lymphedema and diabetes can be prone to deep vein thrombosis (DVT). Post-operative patients are often treated with a DVT cuff during surgery and afterwards for up to 72 hours. Clinicians would prefer to send patients home with DVT cuffs and a treatment regimen to reduce the risk of blood clots. However, patient compliance is often a problem because the traditional DVT cuff renders the patient immobile and uncomfortable during the treatment, which can be an hour or more. Travelers confined to tight quarters during airline travel or long-distance driving, for example, are also particularly at risk for the development of thromboses, or blood clots due to decreased blood flow. Varicose veins are another disorder resulting from problems with patient blood flow. Varicose veins are often a symptom of an underlying condition called venous insufficiency. Normal veins have one-way valves that allow blood to flow upward only to return to the heart and lungs. A varicose vein has valves that are not functioning properly. The blood can flow upwards, but tends to pool in the vein because of valve dysfunction. The varicose veins bulge because they are filled with pooled blood. Although varicose veins are often a cosmetic concern, the condition also causes pain, leg heaviness, fatigue, itching, night cramps, leg swelling, and restless legs at night. Varicose vein disease can be treated with various nonsurgical techniques such as sclerotherapy or endovenous laser treatment (EVLT). In some cases enhanced blood flow is essential for quality of life, such as for those individuals suffering from RVD (peripheral vascular disease) and RLS (restless leg syndrome), or women undergoing reconstructive breast surgery suffering from arm pain and fatigue due to poor blood flow.

For some individuals the condition can also be treated by the nightly use of compression stockings. Compression stockings are elastic stockings that squeeze the veins and stop excess blood from flowing backward. These, and other known devices, tend to only provide an initial compression force at a low level that decreases over time upon continued deformation of the stocking. Moreover, stockings of this type are difficult to put on and take off, particularly for the elderly.

Many athletes, whether professionals or lay persons, suffer from muscle soreness, pain and fatigue after exercise due to toxins and other workout by-products being released. Recent research has shown that compression garments may provide ergogenic benefits for athletes during exercise by enhancing lactate removal, reducing muscle oscillation and positively influencing psychological factors. Some early research on compression garments has demonstrated a reduction in blood lactate concentration during maximal exercise on a bicycle ergometer. Later investigations have shown improved repeated jump power and increased vertical jump height. The suggested reasons for the improved jumping ability with compression garments include an improved warm-up via increased skin temperature, reduced muscle oscillation upon ground contact and increased torque generated about the hip joint. Reaction time is important to most athletes, as well as to race car drivers, drag racers and even fighter pilots. Exercise science and kinesiology experts point to training modules, such as PitFit™, that benefit from acute sensory drills and increased oxygen intake related to increased blood flow. Combined, these results show that compression garments may provide both a performance enhancement and an injury reduction role during exercises provoking high blood lactate concentrations or explosive-based movements.

Research has also shown that compression garments may promote blood lactate removal and therefore enhance recovery during periods following strenuous exercise. In one test, significant reduction in blood lactate levels in highly fit were observed in males wearing compression stockings following a bicycle ergometer test at 110 percent $VO_2$ max. Similar results were obtained in a later study in which a significant reduction in blood lactate concentration and an increased plasma volume was found in twelve elderly trained cyclists wearing compression garments following five minutes of maximal cycling. In another test, wearing compression garments during an 80-minute rest period following the five minutes of maximal cycling were shown to significantly increase (2.1 percent) performance during a subsequent maximal cycling test. It was suggested that increased removal of the metabolic by-products during intense exercise when wearing compression garments may help improve performance. These results suggest that wearing compression garments during recovery periods following high intensity exercise may enhance the recovery process both during and following intense exercise and therefore improve exercise performance.

Compression devices have also been used during recovery periods for athletes following strenuous activity. These devices are generally limited to the athlete's legs and typically comprise a series of inflatable bladders in a heel-to-thigh casing. An air pump inflates the series of bladders in a predetermined sequence to stimulate arterial blood flow through the athlete's legs. Compression devices of this type are extremely bulky, requiring that the athlete remain generally immobile, either seated or in a prone position.

There is a need for improved devices and associated methods for compressing a portion of a patient's or athlete's body, and even an animal's body, such as a race horse or working dog. Of particular need is a device that is comfortable and mobile. Current technology uses plastic (PVC) wrapped around the extremity causing enhanced perspiration and discomfort, so a device that is comfortable and mobile will increase athlete and patient compliance with a treatment regimen. In patients, such compliance may reduce the risk of DVT and/or related peripheral vascular disease (PVD), or venous flow anomalies which could have positive economic impact on costs of healthcare.

SUMMARY

According to this invention the compression device is an apparatus that utilizes shape changing materials in conjunction with elongated compression textiles or fabrics to apply controllable intermittent sequential compression or constriction pressure to a body portion of a person. In one aspect, the shape changing material may be a shape memory metal alloy (SMA) that contracts in response to heat or to an electrical current. In another aspect, the shape changing material may be a phase change material that contracts as the material changes phase.

The compression device incorporates a pre-tensioning element that applies a known initial tension to the shape changing material prior to activation of a compression cycle. In one aspect, the pre-tensioning element is an elastic band, such as a bungee cord, that is connected across the shape changing material element, such as an SMA wire. When the compression device is worn on the body of the user, the pre-tensioning element is placed into tension, which also applies a pre-tension to the SMA wire. The SMA wire is then actuated according to a compression protocol to sequentially contract and release the SMA wire.

The compression devices of the present disclosure can be integrated into articles of clothing, such as pants, hats, athletic shoes, dress shoes, such as high-heel shoes, slippers and socks. The compression protocol applied to actuate the SMA wires, as well as the amount of pre-tension provided by the pre-tensioning element can be calibrated to the particular article of clothing in which the device is integrated.

DESCRIPTION OF THE FIGURES

FIG. 18b is a partial perspective view of the compression device encircling a limb of a user.

FIGS. 19a-19c are sequential views of the compression device shown in FIG. 18 with different SMA wires actuated to generate a peristaltic-like compression.

FIG. 20 is a perspective view of a rib for use in the device shown in FIG. 18.

FIG. 21 is a top view of a rib according to a further embodiment for use in the compression device shown in FIG. 18.

FIG. 22 is a side cross-sectional view of the rib shown in FIG. 21, taken along line 22-22.

FIG. 23 is a side cross-sectional view of the rib shown in FIG. 21, taken along line 23-23.

FIG. 24 is a top view of a compression device according to another aspect of the present disclosure.

FIG. 25 is a cross-sectional view of the device shown in FIG. 24, taken along line 25-25.

FIG. 26 is a top view of a compression device according to yet another aspect of the present disclosure.

FIG. 27 is a view of one face of a strap component of the compression device shown in FIG. 26.

FIG. 28 is a view of an opposite face of the strap component shown in FIG. 27.

FIG. 29 is a cut-away view of the strap component shown in FIGS. 27-28.

FIG. 30 is a top view of an accessory component for use with the compression device shown in FIG. 26.

FIG. 31 is a plan view of the inner assembly of a compression device according to a further aspect of the present disclosure.

FIG. 32 is a plan view of the outer face of the compression device shown in FIG. 31.

FIG. 33 is a plan view of the inner face of the compression device shown in FIGS. 31-32.

FIG. 34B is an enlarged view of an alternative configuration of the tensioner shown in FIG. 34a.

FIGS. 45a, 45b are top perspective views of a compression device integrated into a shoe.

FIG. 45c is an end view in cross-section of the show in FIGS. 45a, b showing components of the compression device.

FIG. 46a is perspective views of a compression device incorporated into a shoe according to one embodiment of the present disclosure.

FIG. 46b is a perspective view of the shoe shown in FIG. 46a with a representation of lines of compression force.

DETAILED DESCRIPTION

Figure 1:
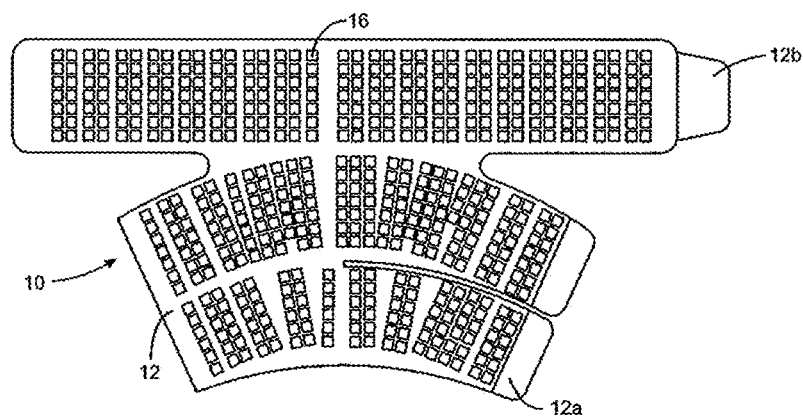
FIG. 1 is a plan view of a compressible fabric body with a plurality of compression pads affixed thereto for use in one embodiment of a device described herein.
Figure 2:
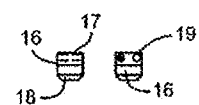
FIG. 2 is an enlarged side and end views of a compression pad shown in FIG. 1.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present disclosure contemplates a compression device that provides the same efficacy for blood flow circulation improvement afforded by current pneumatic arterial constriction devices, but in a device that is not restrictive to the patient or athlete during a compression treatment. Current products require the patient to remain relatively immobile in a seated position or prone while air bladders in the wrap are inflated and deflated. Inflation and deflation of the air bladders requires a bulky external pump and hoses, which effectively ties the user to one location. The present invention contemplates a device that can be easily and comfortably worn while allowing full mobility of the patient or athlete.

One embodiment of compression device 10 is shown in FIGS. 1-5. The device 10 in the illustrated embodiment is configured to be wrapped around the calf, but it is understood that the device can be modified as necessary for treatment of other extremities. The device 10 includes a textile or fabric body 12 having a lower segment 12a configured to fit around the foot of the user and an upper segment 12b configured to encircle the lower leg. The ends of each segment may include a hook and loop fastener arrangement to permit adjustable fit around the user's foot and calf. Other means for adjustably fastening the body segments about the user's body are contemplated, such as an array of hooks, eyelets, zipper, Velcro or similar fastening devices. The fastening devices may also be similar to the tightening mechanisms used in thoracic spinal bracing, backs packs and even shoes. It is further contemplated that the device may be a closed body that is integral around the circumference.

The fabric body 12 may be formed of a generally inelastic or only moderately "stretchable" material that is suited for contact with the skin of the user. The material of the fabric body may be a breathable material to reduce perspiration or may be a generally impermeable material to enhance heating of the body part under compression treatment. It is understood that the configuration of the body 12 shown in FIG. 3 can be modified according to the body part being treated. For instance, the fabric body 12 may be limited to the upper segment 12b to wrap the calf, thigh, bicep or forearm only. The body may also be configured to fit at the knee or elbow of the user. The fabric body may be provided with a "tacky" coating or strips on the surface facing the limb, with the "tacky" coating helping to hold the body against sliding along the user's limb, particularly if the user sweats beneath the fabric body.

In one embodiment, the fabric body can be a compressible body having a thickness to accommodate the shape-changing elements described herein. In another embodiment, the compressibility of the device is accomplished by one or more compressible pads. In the embodiment illustrated in FIGS. 1-3, the fabric body includes an array of pads 16 that are configured to transmit pressure from the device as it is compressed. As explained in more detail herein, the pressure is sequentially applied to certain groups of pads when wrapped around the extremity to apply alternating pressure to specific locations of the patient's or athlete's extremity, such as the ankle and lower calf in the illustrated embodiment. In certain compression protocols, the compression force applied to the user can be as high as 2 psi, although the compression force in most applications is only about 0.5 psi. Thus, the pads are configured to uniformly transmit this range of pressures. In one specific embodiment, each pad is in the form of a 1 cm×1 cm rectangle. The pads may be provided in rows separated by 0.25 cm to about 0.75 cm, and preferably about 4 cm in order to provide an optimum pressure profile to the patient/athlete's limb. Each pad includes an inner portion 17 and an outer portion 18, as shown in the detail view of FIG. 2. In one embodiment, the inner portion is formed of a material to provide a hard generally non-compressible surface, such as a nylon having a durometer value of about 110. The outer portion 18 is formed of a wicking compressible material, such as a soft compressible memory foam that is adapted to lie against the patient's skin. The inner portion 17 is fastened or affixed to the fabric body 12 in a suitable manner, such as by use of an adhesive. The inner portion 17 of each pad 16 is provided with one or more, and preferably two, bores 19 therethrough to receive a shape-changing element as described herein. An additional layer of material may line exposed surface of the inner portion which contacts the extremity surface. For instance, the device may be provided with a soft, breathable sheet of material that is affixed to the fabric body to cover the compressible pads 16. The additional sheet may be removably fastened, such as by hook and loop fasteners at its ends.

Figure 3:
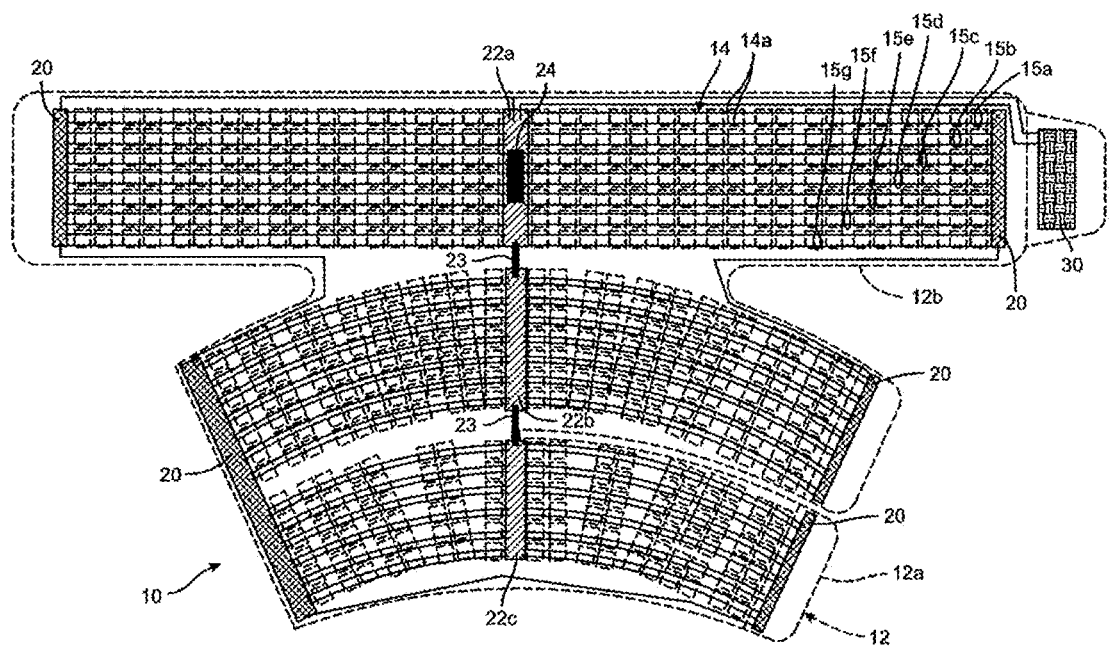
FIG. 3 is a plan view of a device according to one disclosed embodiment.

In accordance with one feature of the present invention, the device is provided with a plurality of shape-changing elements that are operable to change shape in response to an external stimulus. This change of shape effectively reduces the circumference of the device encircling the user's limb, thereby applying pressure or a compressive force to the limb. In one embodiment, the shape-changing element is an element configured to change length, and more particularly to reduce its length in response to the stimulus. In one specific embodiment element is one or more wires formed of a "shape memory" material or alloy that shrinks when a current is applied to the wire, and that returns to its original "memory" configuration when the current is removed or changed. As shown in FIG. 3, the compression device 10 includes a wire array 14 that spans the width and length of each segment 12a, 12b of the fabric body 12, and that extends through the bores 19 in each compression pad 16. The wire array is configured to reduce the diameter of the corresponding segment or portion of a segment when the wire array is activated. In certain embodiments, the wire array can include wires formed of a "memory" material that changes length upon application of an electrical signal and then returns to its original length when the signal is terminate. In a specific embodiment, the memory material can be a memory metal such as Nitinol or Dynalloy wire having a diameter of 0.008 in. In one specific embodiment, the memory wires 14 are configured so that a current of 0.660 amp passing through each wires causes it to shrink sufficiently to exert a force of about 1.26 lbf to 4 lbf In other embodiments, the wire array may be formed of an auxetic material that expands when placed in and then returns to its initial thickness when the is removed.

The fabric body 12 may be provided with pockets or sleeves to receive and retain the compressible pads 16. It is further contemplated that each row of compressible pads is replaced by a single elongated compressible cushion element with the bores 16 passing therethrough to receive the corresponding pairs of memory wires 14a. It is further contemplated that the fabric body 12 may be configured so that the compressible pads or elongated cushion elements are sewn into the body.

As reflected in FIG. 3 each pair of wires 14a passing through a row of compression pads 16, or elongated cushion elements, corresponds to a single channel that can be individually actuated during a compression treatment. Each channel, or wire pair, 14a is connected to a microcontroller as described herein. In the illustrated embodiment, the upper segment 12b includes seven such channels 15a-15g. The lower segment 12a includes a wire array with seven channels and a wire array with six channels. Each row or channel of wires 14a in the wiring array 14 terminates at a negative anode or ground plane 20 at the opposite ends of each body segment 12a, 12b. Each channel, such as the channels 15a-15g, is electrically connected to a corresponding distribution circuit board 22a-22c. A flexible multi-conductor cable 23 connects the distribution circuit boards between segments of the fabric body 12 so that the distribution circuit boards do not interfere with the ability of the device 10 to be wrapped snugly about the user's extremity.

Figure 4:
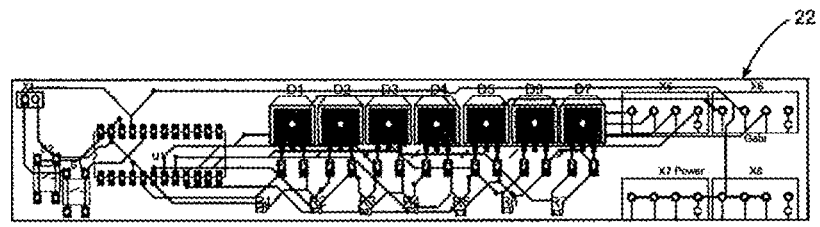
FIG. 4 is a top view of a circuit board for use in the device shown in FIG. 3.

One of the distribution circuit boards 22a carries a microprocessor 24 that controls the sequence and magnitude of the current applied to the memory wires in each channel. As shown in FIG. 4, the distribution circuit boards 22 can include surface mount resistors and power mosfets electrically connected to the wire pairs of each channel. The microcontroller 24 is preferably not hard-wired to the circuit board 22a to permit replacement of one pre-programmed microcontroller with a differently programmed microcontroller. In one embodiment, a microcontroller may be pre-programmed with a particular compression sequence for a particular user and a particular device. For instance, the compression sequence may be an infinite or continuous rolling in which the device is successively compressed along the length of the user's limb similar to a peristaltic movement, a step-wise sequence in which the device is compressed and held for a period, or even a random sequence. Other compression protocols may be preprogrammed into other microcontrollers that can be selected by the user or physical therapist as desired.

Figure 5:
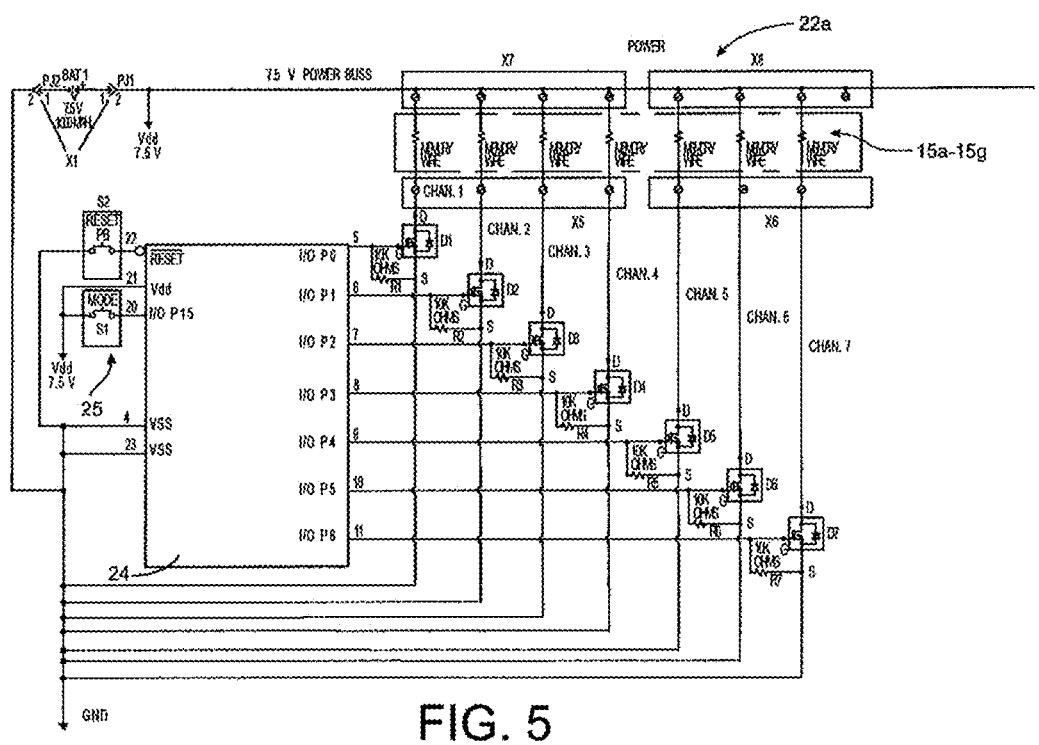
FIG. 5 is a circuit diagram for the electrical circuit of the device shown in FIG. 3.

Details of the circuit board 22a and microcontroller 24 are shown in the circuit diagram of FIG. 5. The microcontroller may be a Parallax microcontroller Part No. BS2-IC, or a Bluetooth enabled Arduino microcontroller, for instance. The microcontroller is provided with a switch array 25 which includes a mode switch S1 and a reset switch S2. The switches are accessible by the user to operate the device 10. Alternatively, the switches may be integrated into a remote communication module capable of wireless communication from outside the compression device. The circuit board may thus incorporate a transmitter/receiver component coupled to the switches S1, S2, such as an RF, Bluetooth, wife or Spec 802.11 device. The device 10 can be equipped with a USB type connection for charging the power supply 30 and for data download or upload. The microcontroller may thus include a memory for storing actuation data, and may further integrate with sensors on the circuit boards that can sense and "report" pressure and temperature, for instance. In one aspect, the microcontroller 24 is thus configured to communicate with a handheld device, such as an iPad, iPod, smart phone, or with another device equipped with wireless transmission/receiving capabilities, such as a PC or laptop computer. The remote device can serve to receive and record actuation data, and can act as a master controller for the micro-controller 24, whether to activate either of the two switches, or in a more advanced configuration to remotely configure or program the micro-controller. The remote device can be used to allow the user to tailor a particular compression protocol. In one aspect, the remote device can implement a software program that allows the user to obtain immediate feedback and provide instructions to the micro-controller 24 in before, during and after a compression sequence. The micro-controller 24 may provide compression readings to the remote device indicative of the amount of compression being applied by the device. In one embodiment, the compression readings can be based on the amount of actuation of the wire array or the current applied to the wire array. The user can use the compression readings during a compression sequence to determine a desirable, or tolerable, amount of compression to program future compression protocols.

A power supply 30 is provided that is connected to the distribution circuit boards 22a-22c and grounded to the negative anodes 20. In one embodiment, the power supply 30 is a 7.5 volt, 40 AH lithium cell array contained with a pouch defined in the fabric body 12. The pouch may be configured to insulate the user from any heat build-up that might occur when the battery is powering the device 10. The power supply 30 is preferably a rechargeable battery that can be recharged through the remote link to the microcontroller described above.

The micro-controller 24 implements software for controlling the sequence and pattern of compression that will be followed through a treatment process. In one embodiment, the micro-controller is activated and controlled by a remote device, as described above. Additionally, the micro-controller can have basic user controls embedded in the device, such as a control panel affixed to the outside of one of the fabric segments 12a, 12b.

The manner in which pressure is applied to the user's body depends upon the number and arrangement of the pads 16 and channels 15. In the illustrated embodiment of FIG. 2, the pads may be actuated from the lowermost channel 15g to the uppermost channel 15a, with successive channels being gradually deactivated, or expanded, and gradually activated, or contracted. Different activation patterns can be pre-programmed into the micro-controller or administered by the remote device as described above. When a channel is activated, the micro-controller 24 directs current to the specific channel which causes the memory wires 14a to contract or shrink, thereby reducing the effective diameter of the memory wires or elongated materials when wrapped around a limb. This reduction in diameter translates to an application of pressure by way of the pads 16 in the same manner as the air-inflatable devices of the prior art. When the current is removed or changed, the "memory" feature of the wire allows it to return to its deactivated or neutral condition, thereby removing pressure from the associated compressible pads. In addition, the limb or fascia acts as a spring to assist in returning the memory wire(s) to the neutral phase.

In an alternative embodiment the multiple 1×1 pads in two or three adjacent rows may be replaced by an elongated compressive pad extending along each side of the fabric body 12. The memory wires 12a are embedded with the elongated pad in the manner described above and each row of elongated compressive pads can be actuated in the same manner as the plurality of smaller pads described above.

Figure 6:
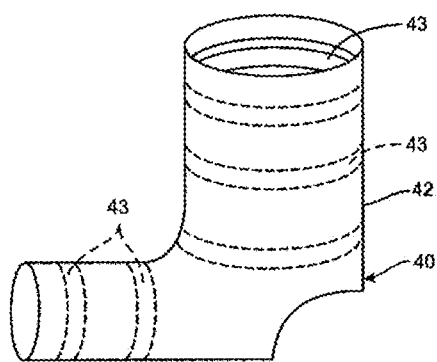
FIG. 6 is a perspective view of an interior sock for a compression device according to one disclosed embodiment.
Figure 7:
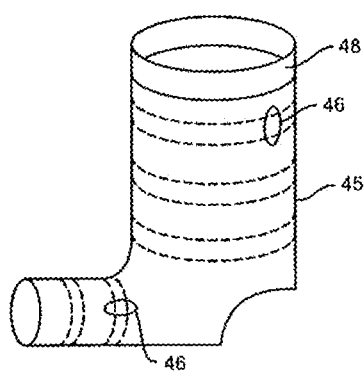
FIG. 7 is a perspective view of an exterior sock for use with the interior sock shown in FIG. 6 for the compression device according to one disclosed embodiment.

In an alternative embodiment, a device 40 may be formed by the combination of an interior sock 42, shown in FIG. 6, and an exterior sock 45, show in FIG. 7. The interior sock 42 incorporates compression pads 43 that encircle the limb and which may be an elongated cushion, as described above, or may be similar to pads 16. The pads 43 may be thermally conductive to convey heat generated by the memory wires to the user's skin. Alternatively, the pads may be thermally insulating to minimize the transmission of heat to the user. The outer sock 45 is integrated over the inner sock 42 and includes the memory wires 46, each aligned with a corresponding pad. The electronics, including the power supply and micro-controller, may be incorporated into a ring 48 at the top of the sock-shaped device 40.

Figure 8:
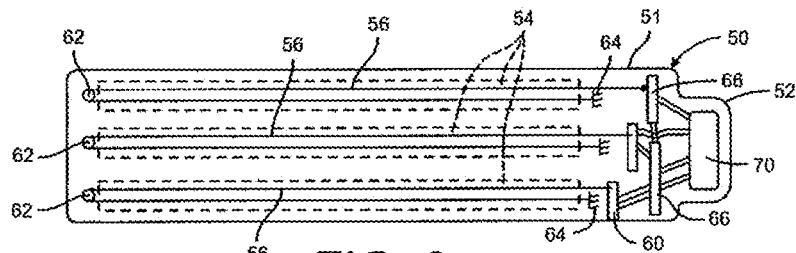
FIG. 8 is a plan view of a device according to a further embodiment utilizing a micro-motor to activate a shape-changing element.

In another embodiment, the shape-changing elements may be replaced by non-extensible wires that are pulled by a motor carried by the device. In particular, an device 50 shown in FIG. 8 includes a fabric body 51 with an extension 52 that may be configured with a fastening feature, such as the hook and loop fastener described above, that engages the opposite ends of the body to wrap the device about a patient's limb. The device may be provided with a number of elongated compressive pads 54 arranged in rows along the length of the fabric body. The pads may be configured as described above, namely to incorporate the bores 19 for receiving wires therethrough. However, unlike the embodiment of FIGS. 1-2, the wires of device 50 need not be memory wires, but are instead generally non-extensible wires 56. One end of each wire 56 is connected to a drive motor 60, then the wire passes through a compressible pad 54, around a pulley 62 at the opposite end of the fabric body 51, and then back through the compressible pad. The end of the wire 56 is "grounded" or fastened to the fabric body 51, as shown in FIG. 8. Each compressible pad includes its own wire 56 and each wire may be driven by its own motor 60. The motors 60 are connected to a micro-controller 66 and to a power supply 70, which may be similar to the power supply 30 described above. The micro-controller is configured to activate each motor 60 according to a prescribed compression protocol.

In order to ensure that the device 50 preserves the mobility and ease of use, the motors 60 may be strip-type motor, such as the Miga Motor Company "HT Flexinol model. The motor is thus compact and adapted for placement across the width of the fabric body 51, as shown in FIG. 8. The motors will not inhibit the compression of the device 50 or otherwise cause discomfort to the wearer. The wires 56 may be plastic wires for low-friction sliding relative to the compressible pads 54, and are generally non-extensible so that pulling the wires translates directly into a compressive force applied through the pads.

In an alternative embodiment, the wires 56 may be replaced by a mesh that is fastened at one end to a corresponding motor 60 and is "grounded" or fastened to the fabric body 51 at the opposite end. In this embodiment, the mesh is "free floating" between the compressible pads and an outer fabric cover. The mesh may be sandwiched between Mylar layers to reduce friction as the mesh is pulled by the motors.

In a further alternative, the motor 60 and wire 56 arrangement shown in FIG. 8 can be modified, as illustrated in FIGS. 9-13. In particular, the wire actuator device 100 shown in FIG. 9 includes a primary circuit board 102 and an overstress protection circuit board 104 supported within a complementary configured cutout 105 in the primary circuit board. The gap formed by the cutout 105 between the circuit boards 102 and 104 enables limited movement of the circuit board 104 independently of the board 102. The primary circuit board 102 includes a power strip 108 that is electrically connected to a power supply, such as the power supply 70 shown in FIG. 8, by way of a connector cable 140. The connector cable 140 may also be configured to electrically connect the wire actuator device 100 to a microcontroller, such as the microcontroller 66 described above. The overstress circuit board 104 is mounted to the primary circuit board 102 by a plurality of resiliently deformable arms or bands 113 that allow some limited relative movement between the two boards 102 and 104 when the motors are operated to actuate the wires. The arms 113 may also be configured to provide a restoring force that opposes tension in the wire 110 to restore the device to its neutral "non-compression" position when power to the wires is removed or reduced.

Figure 9:
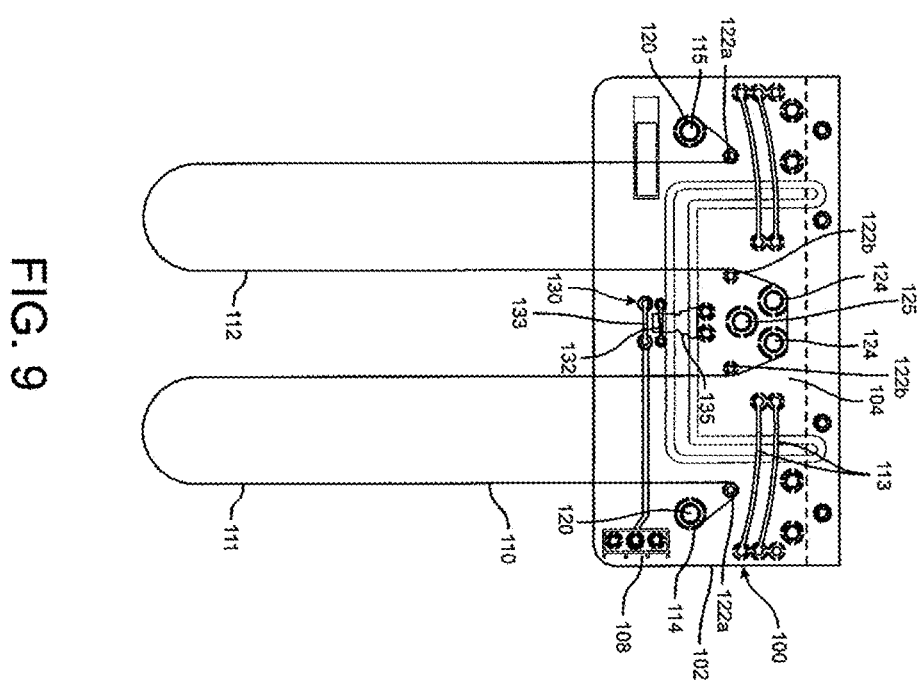
FIG. 9 is a top view of a compression device according to a further aspect of the present disclosure.

In one embodiment, the device 100 includes a shape-changing element in the form of a single wire 110 that is configured to form two loops 111, 112, as shown in FIG. 9. The wire may be the memory wire or shape memory alloy (SMA) as described above. The ends 114, 115 of the wire are anchored to the primary circuit board 102 by suitable means, such as an anchor screw 120 threaded into the circuit board as is known in the art. The wire 110 is looped from the anchor screw 120 over a capstan 122 and into a corresponding loop 111, 112. The loops 111, 112 have a length sufficient to extend along the length of the device, in the manner shown in FIG. 8 for the device 50. The loops may engage a pulley, such as the pulley 62 at an end of the device opposite from the primary circuit board 12. The two loops combine at the overstress circuit board 104, each loop engaging a corresponding capstan 122b and electrically engaging a contact mount 124. In an alternative embodiment, the loops can wrap around the contact mounts 124 and engage an interior contact mount 125. Electrical current is applied to the SMA wire 110 at the contact mounts 124, or 125 to heat the wire ohmically beyond the SMA transition temperature and to cause the wire to change length or contract, thereby applying compression to the device.

Power is supplied to the contact mounts 124 by way of an over-force contact feature 130. The over-force contact feature is operable to disengage power to the wires in the event that the wires become over-tightened. The contact mounts are electrically connected to a contact 135 that is movable with the overstress circuit board 104. In normal operation, the contact 135 is in conductive contact with a power input lead 132 so that power is supplied to the wire 110. However, in an overstress condition in which the wire 110 is over-tightened, the wire tension will deflect the arms 113 and the contact 135 will move into contact with the bypass lead 133 that disengages power to the wire 110. The input and bypass leads 132, 133 thus operate as a switch to terminate power when the switch is triggered by excessive movement of the overstress circuit board due to over-tightening of the wire 110. Over tightening may be caused by the user pulling the body 51 too taut about his/her limb, or during actuation of the device when in use. The overstress feature prevents the tension on the SMA wire 110 from exceeding the tensile strength of the wire to thereby protect the wire from failure.

Figure 10:
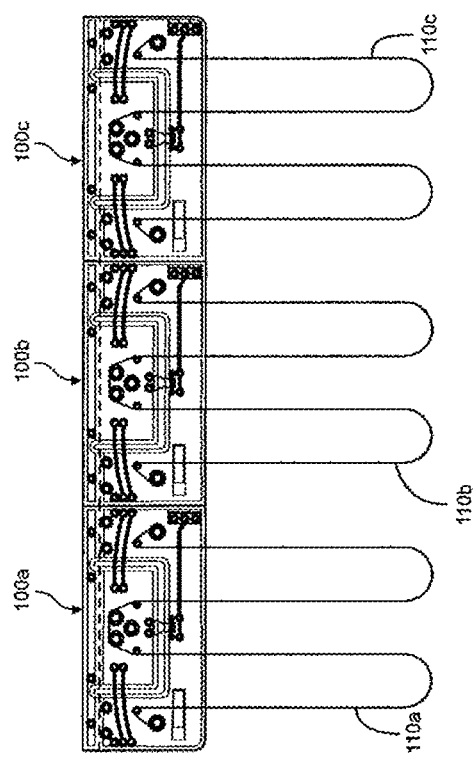
FIG. 10 is a top view of an array of the compression devices depicted in FIG. 9

A plurality of the devices 100 may be provided on a single device, such as spanning the width of the fabric body 51 of an device configured similar to the device 50 described above. Thus, as shown in FIG. 10 three devices 100a, 100b, 100c are provided, each with their corresponding wire 110a, 110b, 110c. Each device may be connected in series or in parallel to the power supply and microcontroller, with each device being separately addressable by the microcontroller to allow each device to be separately actuated. The microcontroller may thus implement a software or hardware routine that activates the devices in a predetermined pattern to achieve a desired compression protocol for the user. For instance, the devices 100a, 100b, 100c may be actuated in a sequence to apply compression to the user's limb sequentially from a distal device to a proximal device (i.e., farthest from the heart to closest to the heart) to in essence push blood upward from the limb.

Figure 11:
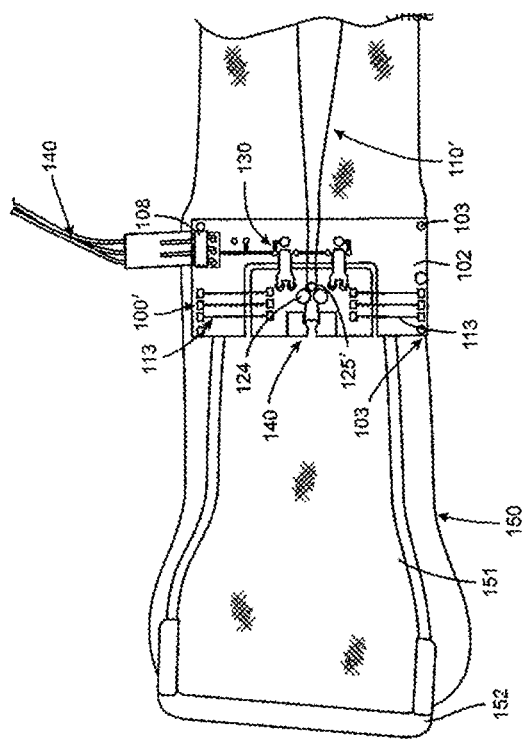
FIG. 11 is a top view of a compression device incorporating a compression device according to a further aspect of the present disclosure.
Figure 13:
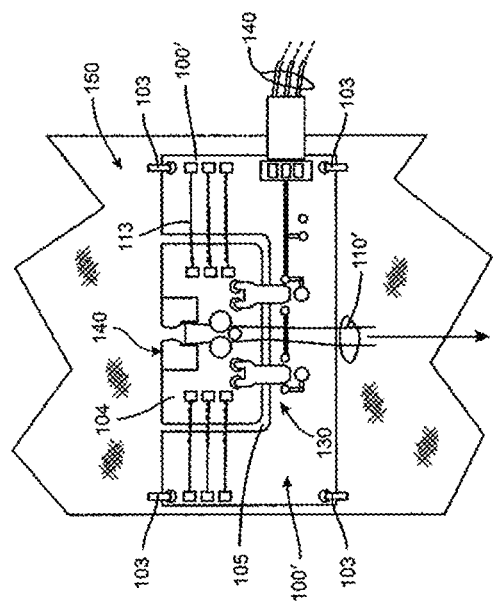
FIG. 13 is an enlarged top view of the primary circuit board and overstress protection board of the compression device of FIG. 11.
Figure 12:
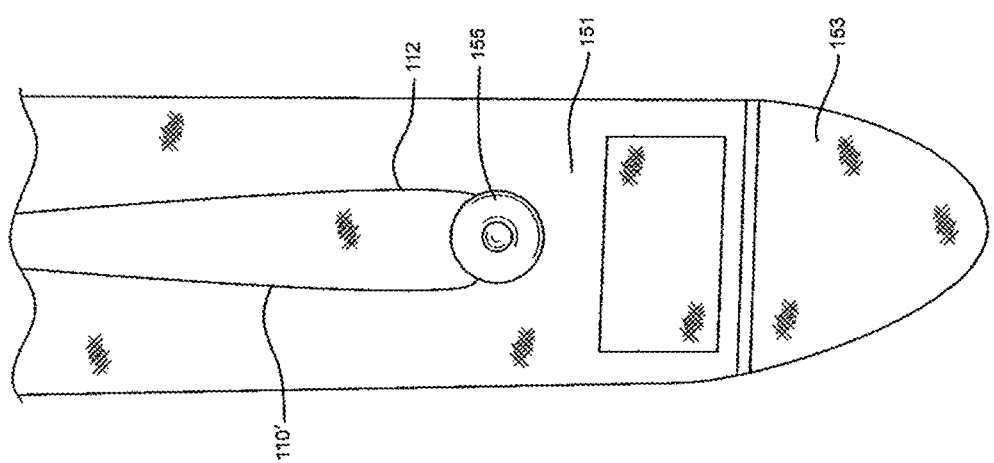
FIG. 12 is an enlarged view of the end of a strap of the compression device shown in FIG. 11.

An exemplary embodiment of a device is shown in FIGS. 11-13. In this embodiment, a single wire actuator device 100' is utilized with a single wire 100' extending from the device 100' at one end of an device wrap 150 to an anchor 155 (FIG. 12) at the opposite end of the wrap. The device 150 includes a fabric strap 151 sized to be wrapped around a limb of a user, such as the calf. The device may include a loop 152 at the device end of the fabric strap through which the opposite end 153 passes. An adjustable length hook-and-loop engagement between the two ends allows the user to wrap the device snugly around his/her limb. It can be appreciated from FIGS. 11-13 that the wire actuator device 100' and wire 110' are disposed on the outside of the fabric strap 151 and not in contact with the user's limb. A fabric cover may be provided to conceal and protect the working components of the device, it being understood that the exposed components in the figures are for illustrative purposes.

As shown in FIG. 11, the wire actuator device 100' is modified from the device 100 in that the wire 110' is anchored on the overstress protection circuit board 104 at posts 140 separate from the capstans 124 and contact mounts 122b. The wire is instead threaded between each capstan 124 and interior capstans 125'. The ends of the wire are fastened to the anchors 140. Threading the wire through the capstans helps eliminate twisting of the wire 110' during actuation and release.

The wire actuator device 100', and particular the circuit board 102, is provided with fastening openings 103 at the corners of the circuit board to accept a fastener for attaching the device to the fabric strap 151. In one embodiment, the circuit board may be sewn to the fabric strap, or held in place by a rivet or snap arrangement. The circuit board is preferably permanently affixed to the strap to provide a solid anchor for the wire 110'. Alternatively the actuator device 100' may be releasably fastened to the strap to provide a fail-safe feature to prevent over-tightening of the wire or cable around the user's limb.

Figure 14:
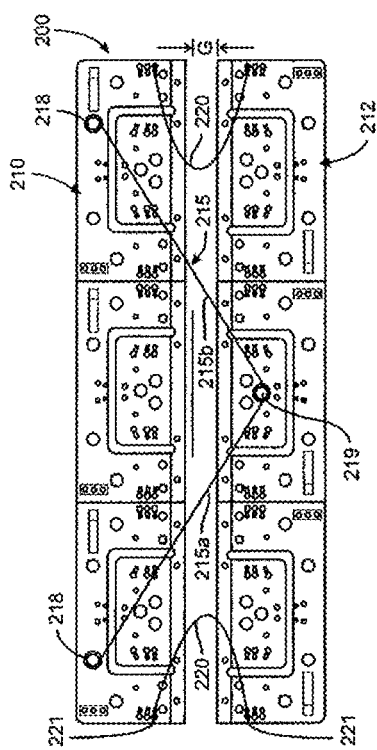
FIG. 14 is a top view of a compression device according to another embodiment of the present disclosure.

A compression device 200 according to a further feature of the present disclosure is shown in FIG. 14. The device 200 includes a pair of ribs 210 and 212, which may be similar to the multi-device circuit board shown in FIG. 10. The ribs are fastened to a device strap, such as the strap 150, separated by a gap G. Unlike the device of FIG. 10, the compression device 200 operates by bringing the two ribs 210, 212 together or closing the gap G. To accomplish this result, a shape-changing wire 215 is connected between the two plates. In one embodiment, each leg 215a, 215b of the wire 215 is fastened to the rib 210 at an anchor mount 218. The wire 215 passes around a capstan 219 mounted on the associated overstress protection circuit board 204 of an adjacent rib 212. Alternatively, each leg 215a, 215b may be fastened to an anchor mount at the location of the capstan 219; however, it is preferable that the wire 215 be free to move around the capstan to ensure uniform movement of the opposite ends of the rib 210 toward the rib 212.

The compression device 200 includes a pair of spring elements 220 fastened to opposite ends of each plate 210, 212 and spanning the gap G. The spring elements are thus anchored at their ends 221 to a respective plate. The restoring force of the spring elements 220 opposes the contraction of the wires 215 and provides a biasing force to restore the ribs to their neutral position with the gap G. The spring elements may be in the form of a V-spring, hammer spring, leaf spring, a resiliently compressible material, or similar type of element capable of pushing the ribs apart when the wire 215 is relaxed.

Figure 15:
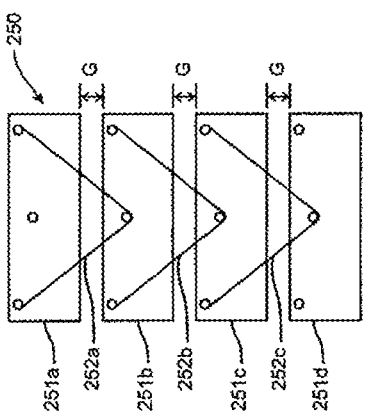
FIG. 15 is a diagram of an array of compression device as shown in FIG. 14.

The example shown in FIG. 14 includes two ribs and a single wire 215 separated by a gap G. In one embodiment, the gap G may be about 0.25 inches. The wire 215 may be a memory metal wire capable of a length reduction of about 0.5 inches, so that full actuation of the wire is capable of substantially fully closing the gap G. As with the previous embodiments the compression device 200 is fastened to an device of fabric strap configured to encircle the limb of a user. It has been found that the configuration of compression device 200 shown in FIG. 14 is capable of producing a compression pressure of about 30 mmHg (assuming that the fabric strap is generally inelastic). It is contemplated that greater pressures may be obtained by adding further ribs and wires. Thus, as depicted in the diagram of FIG. 15, a compression device 250 may be formed by four ribs 251a-251d, each fastened to a fabric strap with a gap G spacing between each plate. Three wires 252a-252c are engaged between adjacent ribs. Each wire is capable of closing the respective gap G, so that the total compression is equivalent to closing a gap of 3×G, or 0.75 inches in the specific embodiment. This leads to an equivalently greater reduction in diameter of the device, which leads to an effective compression pressure of about 90-100 mmHg for the specific example. Of course, additional ribs and wires can be added in series with the four ribs shown in FIG. 15, to thereby increase the maximum compression pressure capability of the device. It is contemplated that typical treatments for human users may invoke compression pressures of 30-150 mmHg.

The multiple wires may be controlled by a common microcontroller, such as described above. The microcontroller may implement instructions to control how many of the wires are activated to thereby control the compression pressure. It is further contemplated that this series array of ribs and wires of the device 250 may be repeated across the width of a given device. These additional devices 250 would be controlled in the same manner by the micro-controller to adjust the amount of pressure applied, and may also be controlled as discussed above to vary which row of the device is activated and to what degree. For instance, for a calf device, three rows of devices 250 may be provided along the length of the calf. The distalmost row (i.e., the row closest to the ankle) may be activated first, followed by the next adjacent rows in sequence to effectively "push" blood upward from the calf. The devices may be activated and released in a predetermined sequence to form a pressure "wave" up the user's leg. In other words, the rows of devices may be actuated to form an infinite scrolling sequence or wave of pressure, as opposed to simply a series of sequential compressions. A series of "waves" may be generated by alternatingly activating alternating rows—i.e., rows 1, 3, 5, etc. are activated while rows 2, 4, 6, etc., are idle, and then the odd numbered rows are deactivated while the even numbered are activated. Alternatively, each row may be maintained in their actuated state, but the amount of pressure can be adjusted along the user's calf. It can be appreciated that the multi-component compression device 250 provides a great deal of flexibility in the compression regimen to provide a treatment tailored to the user and the condition being treated.

Figure 16:
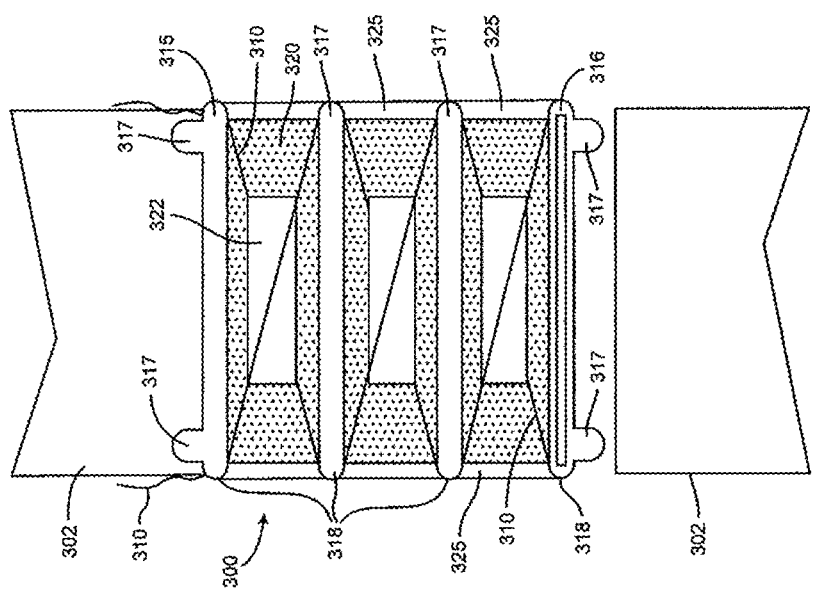
FIG. 16 is a diagram of a compression device according to yet another embodiment of the present disclosure.

A compression device 300 is shown in FIG. 16 that essentially provides a mechanical advantage for a given length change of a wire 310. In this embodiment, the wire is laced along the fabric strap 302 around support ribs 315, 316 and 317. The endmost ribs 315, 316 are provided with anchors 317 for attachment to the strap 302. The wire 310 may be sized to extend along substantially the entire length of the strap 302, like the wire 110 in FIG. 9, or may be limited to the space between the endmost ribs 315, 316. As shown in FIG. 16, the wire 310 winds around the ends 318 of the ribs and around the endmost ribs 315, 316. The wire crosses over itself in the space between the ribs, similar to lacing a shoe. A spacer 322 is included between the crossing portions of the wire to eliminate friction between the portions as the wire contracts and expands. An insulator panel 320 may be provided between the wire 310 and the strap 302 for thermal and electrical isolation.

Resilient elements 325 are provided between the ribs 315, 316, 317 that are configured to resiliently deflect when the wire 310 contracts and to flex back to their neutral shape when the wire is deactivated. In one embodiment the resilient elements may be in the form of a leaf spring or a bow spring between each rib. Alternatively, a single resilient element may extend along each side of the device 300 with the ribs affixed at spaced-apart locations on the resilient element 325.

In another embodiment, the compression device can be formed with a series of ribs with tensioning elements spanning between plates in a manner to increase the mechanical advantage for a given change in length of the tensioning elements. In one embodiment shown in FIG. 17, a compression arrangement 350 is provided that can be extended partially or entirely around the entire circumference of the compression device or can be integrated into a fabric strap, such as in the manner depicted in FIG. 16. The compression arrangement 350 includes two ribs 351a, 351b, although more plates may be utilized. The ends of a first SMA wire 352a are anchored to the plate 351a at anchors 353a, 354a. The SMA wire 352a passes over pulleys 355a, 356a at the opposed ends of the rib 351a, respectively. The first SMA wire 352a extends to an adjacent rib (not shown) or to an anchor affixed to a fabric strap, such as strap 302.

A second SMA wire 352b passes around pulleys 357a, 358a at opposite ends of the first rib 351a. The second SMA wire extends to the second rib 351b to pass around pulleys 355b, 356b and is anchored at 353b, 354b. A third SMA wire 352c is connected to the second rib 351b across pulleys 357b, 358b. The anchors 353a, 354a, 353b, 354b also provide the point of electrical connection for the shape-changing SMA wires discussed above. Each rib may thus include its own circuit board for controlling current to its respective SMA wire, or the ribs may be wired to a common controller.

It can be appreciated that the two ribs 351a, 351b are identically configured so that multiple such ribs 351 can be daisy-chained together with SMA wires 352 to increase the compressive capability of the compression device. Moreover, the contraction of each SMA wire 352 along its entire length is applied uniformly to the gap between adjacent ribs 351. In other words, in a specific embodiment if the SMA wires 352 between each pair of ribs can undergo a change in length or contraction of 0.25 in., then combining four such plates can result in a combined 1.0 in. contraction between the ribs, which as a consequence results in a greater compressive force around the patient. In essence, this feature of the multiple ribs provides for a displacement multiplication of the assembled ribs, which results in a much greater tangential constriction for the device. Each rib 351 can be actuated discretely or in any combination or sequence as desired to create a compression profile.

The compression assembly 400 shown in FIG. 18 is similar to the assembly 350 in that it improves the mechanical advantage for the SMA wire arrangements. In this embodiment, each rib 401 (401a, 401b, 401c) supports a portion of four SMA wires. For instance, rib 401a supports wires 402a, 403a, 402b and 403b, while rib 401b supports wires 402b, 403b, 402c and 403c, and rib 401c supports wires 402c, 403c, 402d and 403d. It can be appreciated that the wires 402 are arranged to span the gaps between like ends of the ribs 401 (i.e., the top end in FIG. 18) while the wires 403 are arranged to span the gaps between the like opposite ends of the ribs 401. The ends of the SMA wires are affixed to the corresponding plate by corresponding anchors, such as anchors 404a, 405a, 406a and 407a for plate 401a, and similar anchors 404-407 for the other ribs in the device. The wires also extend around associated pulleys, such as pulleys 408a, 409a, 410a and 411a on plate 401a, and corresponding pulleys 408-411 for the other ribs in the device. The anchors and pulleys may be configured similar to the embodiment of FIG. 17.

Figure 18A:
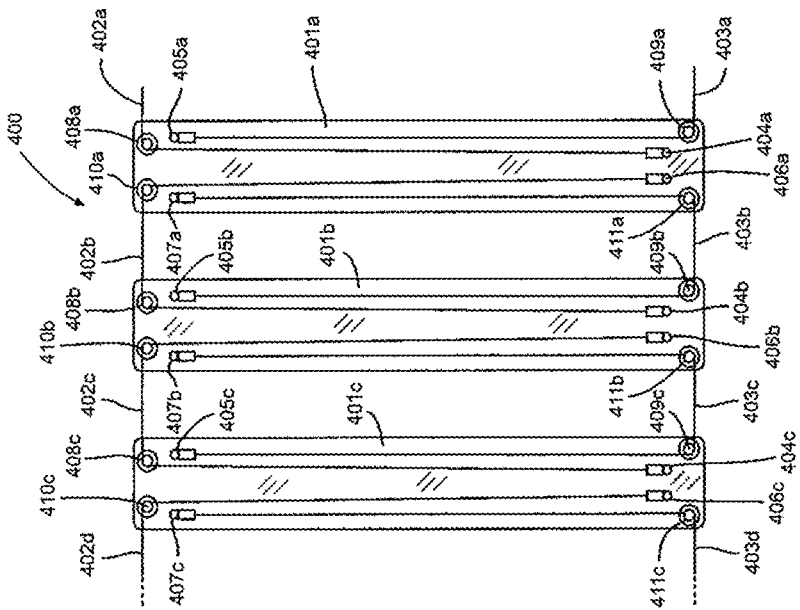
FIG. 18a is a top view of a compression device according to another aspect of the present disclosure.

As shown in FIG. 18a, two wires 402b and 403b extend between the same pair of plates 401a and 401b. The SMA wires in the compression assembly 400 essentially form an overlapping daisy-chain, as opposed to the single daisy-chain arrangement of the compression assembly 350. This overlapping daisy-chain arrangement provides the mechanical advantage or displacement multiplication improvement of the prior embodiment, particularly when more than two ribs are provided. In addition, this overlapping daisy-chain allows for a non-uniform compression pattern across the span of the ribs (i.e., from top end to bottom end as viewed in FIG. 18a). In particular, with this arrangement, any single SMA wire, such as wire 402b, can be actuated so that the top ends of the ribs 401a, 401b will be drawn together while the bottom ends of the ribs are inactive. Alternatively, all of the upper SMA wires 402a, 402b, 402c, 402d can be actuated or all of the lower SMA wires 403a, 403b, 403c, 403d (or any combination thereof) may be actuated to draw the top or bottom of the ribs together.

For instance, as depicted in FIGS. 19a-19c the device 400 may be actuated to generate a peristaltic-type compression displacement of the ribs. In FIG. 19a, only the SMA wires 402a, 402b, 402c, 402d spanning the gaps between the left ends of the respective ribs are actuated so that the like ends (i.e., left side in the figure) of the ribs are drawn together. The compression applied by the device 400 is thus limited to the left side of the ribs. In FIG. 19b, the SMA wires 403a, 403b, 403c, 403d at both ends of the ribs are actuated or contracted, essentially drawing the right sides of the ribs 401a, 401b, 401c together so that compression is applied essentially evenly across the entire width of the compression device 400. Then in FIG. 19c, the upper SMA wires 402a, 402b, 402c, 402d are released so that the compression is released at the left ends of the ribs. Next the right side SMA wires 403a, 403b, 403c, 403d are relaxed so that the device 400 returns to its neutral configuration depicted in FIG. 18. This sequence can be repeated during a compression protocol.

It can be appreciated that this overlapping daisy-chain arrangement combined with the displacement multiplication arrangement adds a greater ability to tailor a compression regimen not only circumferentially around the patient's limb, but also axially along the length of the limb. Providing a series of the compression assemblies 400 axially along the length of the limb adds an even greater degree of variability to the compression regimen.

Figure 17:
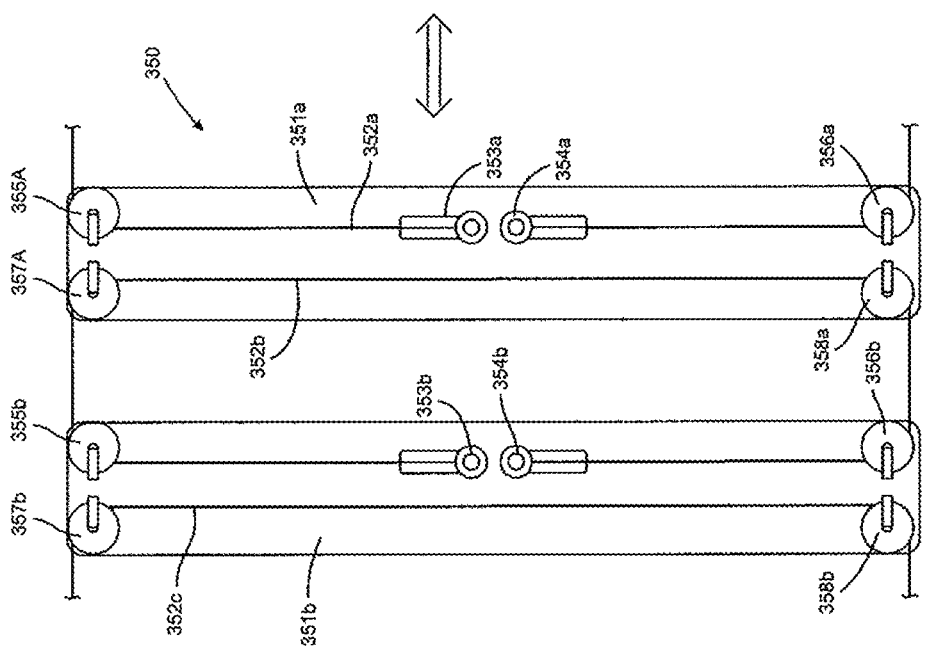
FIG. 17 is a top view of a compression device according to a further aspect of the present disclosure.

In the embodiments of FIGS. 17-18, the pulleys, such as pulleys 355a and 408a, may be wheels or discs that are rotatably mounted, 3D printed or overmolded onto the respective rib. In an alternative configuration, the rib may be configured to provide bearing surfaces for the SMA wires. Thus, as shown in FIG. 20, a rib 401 may be molded to integrally define outer ribs 412 and 414 that have curved ends 413, 415, respectively. The curved ends correspond to the pulleys 408a, 410a of the compression assembly 400, for instance. Similarly, interior ribs 420 and 424 are provided, each having a curved end 421, 425, respectively. The curved ends correspond to the pulleys 409a, 411a, for instance. Openings, such as opening 428, may be provided in the rib 401 for anchoring the ends of the SMA wires.

Another approach is shown in FIGS. 21-23. The rib 450 may be similar to the ribs in the embodiments of FIGS. 17-18. In particular, the rib 450 includes a substrate 451 that may be conventional for circuit boards and the like. However, rather than providing separate anchors, such as anchor 405a shown in FIG. 18, the rib 450 shown in FIG. 20 incorporates a clamp plate 454 at each end of the rib that spans the width of the rib. As shown in the cross-sectional view of FIG. 22, the clamp plate 454 includes alternative V-shaped slots 456 and circular slots 457. The V-shaped slots 456 are sized to allow a SMA wire, such as wires 403a and 403b in FIG. 21, to slide with little resistance. The circular slots 457, however, are configured to clamp the end of a corresponding wire, such as wires 402a, 402b. Thus, as can be appreciated from FIG. 21, the wires 403a, 403b are clamped at the lower end of the rib 450 while the wires 402a, 402b must be free to translate as the wires contract and expand. The clamp plate 454 is also mounted at the top of the rib, but is re-oriented 180° so that the ends of the wires 402a, 402b are being anchored and the other wires 403a, 403b are free to slide. The clamp plate 454 may be fastened to the rib 450 by screws 455, a bonding agent or other suitable fasteners.

In another aspect of the rib 450, the pulleys of the prior embodiments are replaced by a guide plate 460. The guide plate 460 defines curved guide slots 463 (see FIGS. 21, 23) that provide a sliding surface to guide the SMA wires laterally from the ribs to interact with an adjacent rib. A guide plate is provided at each end of each rib and may be engaged by screws 461 or other suitable fasteners.

A compression device 500 shown in FIGS. 24-25 utilizes two SMA wires to accomplish the compression function. The device 500 includes a plurality of ribs 501 arranged on an elongated body as described above. Each of the ribs is a multi-layer construction, as depicted in FIG. 25 with a center panel 510 sandwiched between opposite panels 512, 514. The panels 510, 512, 514 define internal arcuate surfaces about which each SMA wire 502a, 502b is wound. In FIG. 24, the ribs 501 are depicted with the upper panel 514 removed to expose the first SMA wire 502a wrapped around arcuate surfaces 520 facing each side 501a, 501b of the rib and adjacent a first end 501c of the rib. The panels 510, 512, 514 further define an internal central arcuate surface 525 which can be in the form of a cylindrical hub. The wire 502a is wrapped around the central arcuate surface, which acts as a pulley surface for sliding movement of the wire 502a. Thus, as shown in FIG. 24, the SMA wire 502a enters the upper most rib 501 at one side 501a, traverses the first arcuate surface 525, wraps around the central arcuate surface 525 and exits the rib 501 via a second arcuate surface 520. The wire 502a repeats this configuration through each successive rib 501.

The multi-layer construction of the rib 501 provides a similar structure for the second SMA wire 502b. As shown in FIGS. 24-25, the arrangement of the first wire 502a overlaps the arrangement of the second SMA wire 502b. The second wire 502b enters the ribs 501 at the opposite end 502d, passing around arcuate surfaces 520 adjacent the opposite sides 501a, 501b of the ribs and extending around a central arcuate surface 525 at the end 501c of the rib.

In operation, each SMA wire 502a, 502b is separately controllable, as described above. When one wire, such as wire 502a, is activated, the wire contracts in length so that the ribs essentially slide relative to the wire 502a to be drawn together at the end 501c of each rib. A similar action occurs when the second wire 502b is actuated. Since the wires are not constrained within the ribs 501, a single wire can be used to contract each end of the compression device. The two wires can be actuated in a predetermined sequence to achieve a pulsing compression as desired.

The compression devices disclosed herein may be provided in a multi-component configuration. For example, as shown in FIGS. 26-30, a compression device 600 may be provided with a base panel 602 with an engagement surface 603, such as a hook-and-loop fastening surface. A pair of elongated panels 610 are provided, with each panel including a number of the plurality of ribs and at least two shape-changing wires, such as any of the rib and wire configurations described above. The elongated panels 610 are provided with an inward surface 612 configured to contact the user's skin, with the surface having a gripping texture to prevent slipping of the device in use. One end 614 of each panel is configured for attachment to the base panel 602, as depicted in FIG. 26. The opposite end 615 of each elongated panel is also configured for attachment to the base panel 602 when the device 600 is wrapped around the body of a user. The ends 614, 615 may be configured with a hook-and-loop fastening feature.

As shown in the partial cut-away view of FIG. 29, each elongated panel 610 includes an array of ribs 630 with SMA wires (not shown) that are connected to electrical couplings 625. The couplings 625 electrically connect the SMA wires of the two elongated panels 610 and can provide electrical connection to an external component, such as an external controller for controlling actuation of the SMA wires as described above.

In a further feature, the elongated panels 610 may be provided with a pre-tensioning element 620 configured to apply a tension across the panel when the device is engaged around a portion of the body of the user. The tensioning element 620 may be connected to one of the ribs 630 by cables 622 that are adapted to be placed in tension by the element 620. In one embodiment, the tensioning element 620 may be a rotating ratchet mechanism configured to wind the cables 622 to thereby place them in tension. The tensioning element 620 allows the user to apply some pre-tension to the device when worn. The pre-tension is maintained as the SMA wires are actuated. This feature thus allows the user to provide two stage compression, with the first stage provided by the tensioning element 620 and the second stage provided by the SMA wires. This two-stage tensioning thus allows for a greater maximum compression than with the SMA wires alone and thus accounts for the compression limits inherent with the SMA feature.

In an additional feature, the compression device 600 may be provided with a removable pouch 640 shown in FIG. 30. The pouch 640 may be removably mounted to the base panel 602, such as at a location 605. The pouch 640 may be configured to receive a cooling or heating element 642 as desired by the user.

A compression device 700 shown in FIGS. 31-33 includes a compression assembly 702 mounted on a flexible panel 704 similar to the shape-changing compression assemblies described above. In one particular embodiment, the compression assembly 702 can include a plurality of SMA wires 705 extending along the length of the device The compression assembly 702 includes cables 703 that are configured to mate with cables 716 of a control module 715 (FIG. 32) that may be held in a pocket 717 on the outer surface of the compression device 700. The control module 715 may be configured to provide a user interface for controlling the compression device or may simply incorporate a power supply, on/off button and wireless interface for communicating with a separate computer as described above.

Figure 34A:
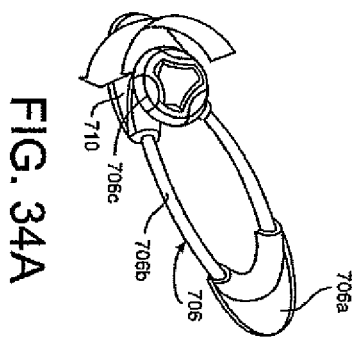
FIG. 34A is an enlarged view of a tensioner used in the compression device shown in FIGS. 31-33.

The panel 704 is thus configured to encircle a body portion, such as a limb, of a user in the manner described above. However, in a modification from the prior embodiments, the panel 704 includes quick-release connectors 708, 709 (FIGS. 31-32) that can be readily snapped together and released. One connector component 709 is affixed to a strap 710 that is integrated into a tensioning component 706. In one embodiment, the tensioning component may be a BOA closure system of BOA Technology, Inc. Details of the BOA closure system can be found in U.S. Pat. No. 8,516,662 (the '662 patent), which issued in Aug. 27, 2013, the disclosure of which is incorporated herein by reference. The BOA closure 706 as generally illustrated in FIG. 34A includes an anchor 706a that is affixed to the panel 704 and a tension dial component 706c that is affixed to the strap 710 connected to the quick-release connector component 708. The tension dial component shortens or lengthens the cable 706b as described in the '662 patent to thereby adjust the tension in the cable 706b. The tensioning component thus provides a mechanism for the user to tighten the compression device 700 to a comfortable fit prior to activating the compression assembly 702. The tensioning component 706 provides the two-stage compression capability discussed above.

Figure 34B:
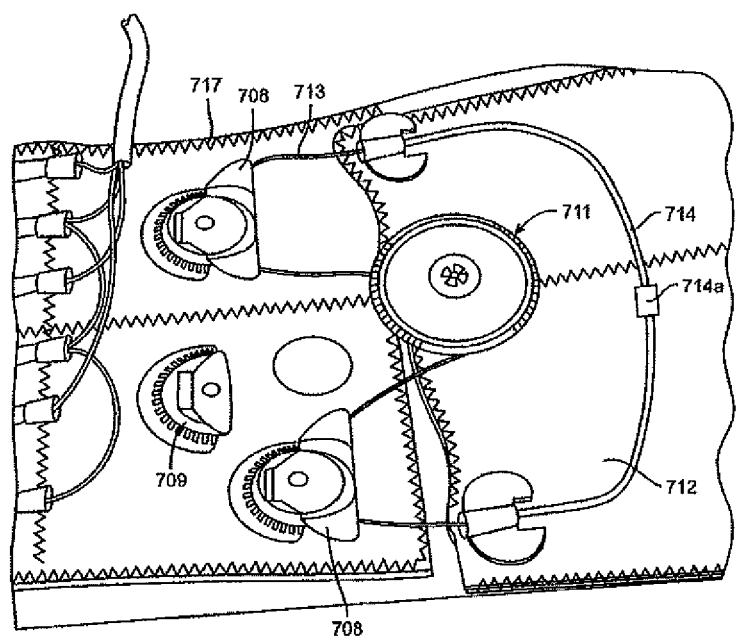

An alternative configuration using the BOA closure is depicted in FIG. 34B. In this configuration, the tension dial component 711 is affixed to one end 712 of a compression device with the cable 713 wound through the tension dial and through two quick-release connector components 708. The cable 713 further passes through a sheath 714 that is partially anchored to the compression device at location 714a. The two connector components 708 are configured to mate with corresponding components 709 that are affixed to an opposite end 717 of the compression device. It can be appreciated that the single tension dial component 711 can apply tension through two quick-release connector components 708/709 with this alternative configuration.

As a further alternative, the SMA wires themselves may be integrated into the BOA closure mechanism, rather than a separate cable, such as cable 713. In this alternative, the SMA wire, such as the SMA wires 705 shown in FIG. 31, the wires 110a-c described in connection with FIG. 10, or the SMA wires shown in the embodiments of FIGS. 8 and 9. Thus, rather than a separate cable passing through the quick-release components 708, 709 and through the tension dial component 711, the SMA wires, such as wires 705 can pass through those components. In this approach, the SMA wires are necessarily longer than in the other embodiments. Preferably, the SMA wires are "wavy" in their unstressed configuration as illustrated by the wires 705' shown in FIG. 34C, rather than generally linear as shown in FIG. 31. The "wavy" wires 705' allow the slack in the wires to be taken up as the tension dial component is rotated. At the same time, the body of the compression device, such as panel 704, is stretched until the slack in the SMA wires is removed. The pre-tensioning thus applies tension to both the panel 704 and the SMA wires 705', with the wires being further tensioned during the operation of the compression device.

Figure 34C:
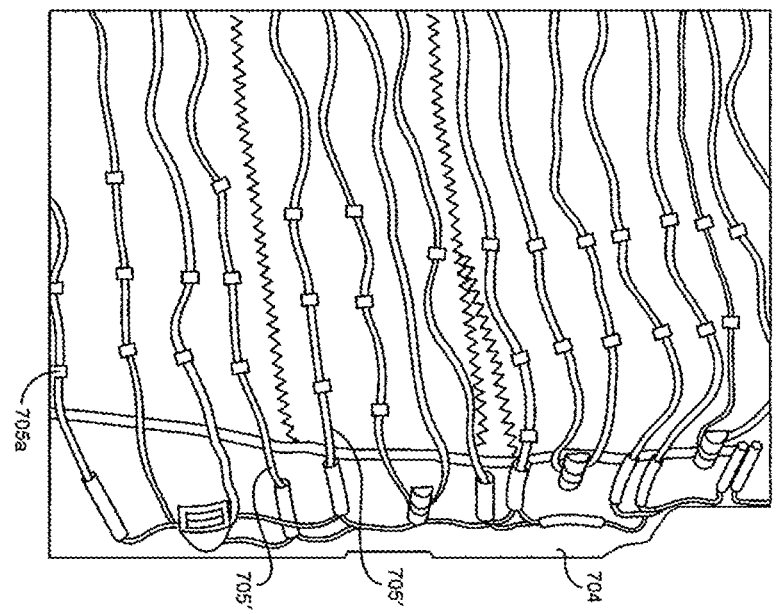
FIG. 34C is an enlarged view of SMA wires in an alternative configuration of the tensioner shown in FIG. 34B.

FIG. 34C illustrates a further feature, namely anchors 705a used to anchor the SMA wire 705' to the body or panel 704 of the compression device. The anchors hold the wires to the panel while allowing the wires to slide as the wires are tensioned and released. In one embodiment, the anchors 705a are loops fastened or sewn to the panel 704 are spaced locations along the length of the device. The anchors 705a are spaced far enough apart to allow the SMA wires to assume the "wavy" shape shown in FIG. 34C, but are also spaced close together enough to provide support the wires as they are activated.

Returning to FIG. 33, the inner face of the compression device 700 may include an athletic mesh inner liner 720. An elastic mesh sleeve 722 may be affixed to the ends of the panel 704 to form an opening through which the user inserts the body part being treated. The sleeve 722 is elastic enough to fit the body part, such as a leg, to help position the compression device 700 prior to fastening the quick-release connectors 708, 709. The inner liner 720 may include a series of sleeves 724 sized to receive heating or cooling strips to enhance the treatment with a form of thermal therapy.

As shown in FIG. 32, the outer face of the device 700 may include a pocket for storing the control module 715. In addition, a panel 718 may be provided on the outer face that allows the user to record information pertinent to the use of the compression device. In one embodiment, the panel 718 may be a dry-erase surface onto which the user may record a particular treatment protocol.

In the disclosed exemplary embodiments, the wires are arranged generally parallel to the extent of the device or fabric strap. In other words, the wires are arranged around parallel circumferences encircling the limb of the user. In alternative embodiments, the wires may be arranged at an angle relative to the circumference. With this configuration, the compression pressure applied by the device when actuated extends not only circumferentially around the limb but also includes a pressure component along the length of the limb. It is further contemplated that the wires may be coated or housed within a tube to help reduce the heat transmission as the wires are actuated. The coating or tubing may be formed of aramid, nylon, TEFLON or other similar low friction, and preferably low thermal conductivity, material.

In the disclosed exemplary embodiments, the compressive force is created by activation of a shape-changing element, whereby under a certain stimulus the element changes shape in a direction adapted to tighten the device about the user's limb. In some embodiments the shape-changing elements are single strand wires, such as memory metal wires, that are activated by flowing a current through and thus ohmically heating the wire. In other alternatives, the shape-changing elements may be braided wires that are activated by an ohmically heated wire passing through the interior of the braid.

In a further alternative, the shape-changing element may be an auxetic cable that changes aspect ratio rather than length. With this type of material, the thickness of the cable increases when the cable is activated, which translates into a radial pressure on the limb for a generally inelastic device. The auxetic cable is actuated by pulling the ends of the cable. A shape memory actuator may be utilized to provide the force to pull the ends of the auxetic cable. It is further contemplated that a micro-solenoid structure may be used to provide the pulling force. In this case, the micro-solenoid can be controlled to provide an oscillating pressure, such as by rapidly pulling and releasing the auxetic cable.

While the present disclosure is generally directed to human users, patients or athletes, the compression devices disclosed herein can be adapted to other animals. For instance, race horses often receive pre- and post-race treatments similar to those received by human athletes. Any of the compression devices disclosed herein may be sized and configured to encircle any part of the leg of a horse. Similar modifications can be made for treatment of other animals as well.

Moreover, the SMA wires described herein may be actuated by the application of an electrical current, such as a typical shape memory alloy. The SMA wires will thus generate heat as the current flows through the wires. This heat may be part of the treatment regiment using the compression devices of the present disclosure. Alternatively, the SMA wires may be thermally isolated to avoid heat transfer to the patient.

As a further alternative, the compression devices or devices disclosed herein can be configured to apply focused pressure on a portion of the body without encircling the body. For instance, a device such as the device 400 may include a limited number of ribs, for example the three ribs shown in FIG. 18. The ribs may be removably adhered to the skin of a patient, such as across or along the lower back. Actuation of the SMA wires cause the space between ribs to successively reduce and expand as the wires contract and return to their neutral length. This action in effect kneads the skin as the device contract and expands. This approach allows the compression devices disclosed herein to be used as a training aid in which the device is worn by an athlete and is controlled to apply a compression force in response to an improper motion. For instance, the device can be adhered the triceps region of the arm of a golfer to apply a compressive force to the back of the arm in response to the golfer's elbow not being straight during a swing. Sensors associated with the device can determine the attitude of the golfer's arm and the relative position of the forearm and upper arm. The slight compressive force applied by the device can cause the golfer to tighten the triceps to thereby straighten the arm. Practice with the compression device generates a muscle memory so that the golfer learns to keep the elbow straight during a swing. The device can be used at any joint of the body to promote proper form for any type of repetitive sports motion, whether kicking a soccer ball, shooting a basketball or executing a butterfly swimming stroke.

The compression devices disclosed herein may be used in Enhanced External Counterpulsation Therapy (EECP) as non-surgical treatment for angina. One or more devices may be wrapped around the lower extremities of a patient to physically squeeze blood back to the heart on each heart beat. The controller of the devices may be linked to or incorporate a pulse sensor that evaluates the heart beat of the patient and then times the activation of the SMA wires to provide compression at an appropriate time in the heart beat cycle. The controller can then operate according to one of the protocols described above in which sections of the compression devices are actuated in sequence to help push blood back to the heart.

Figure 35:
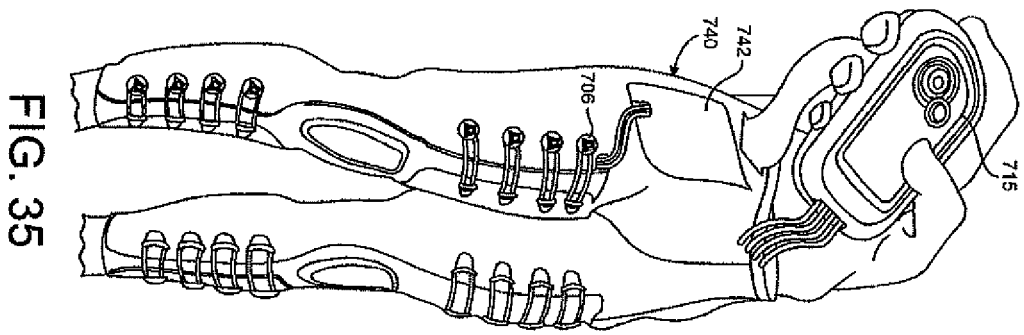
FIG. 35 is a perspective view of a full lower body compression device according to one feature of the present disclosure.
Figure 36:
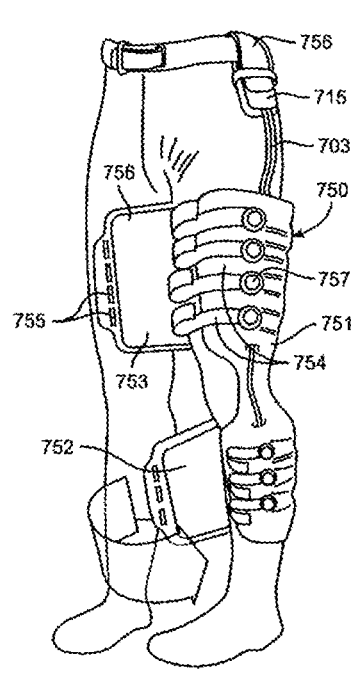
FIG. 36 is a perspective view of a single leg compression device according to a further feature of the present disclosure.
Figure 37:
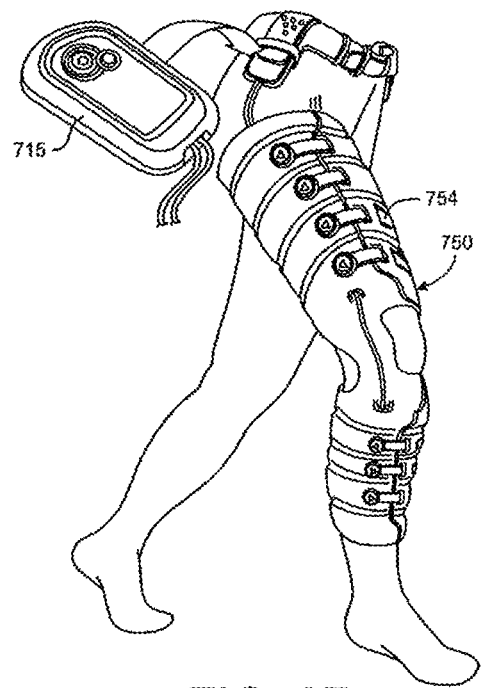
FIG. 37 is a perspective view of the single leg compression device of FIG. 36 shown wrapped around a user's leg.

The compression devices disclosed herein may be used to treat nearly all muscles of the body. As shown in FIG. 35, the compression device can be integrated into a wearable full lower body compression device 740 with compression applied at each leg 706. A pocket 742 can be incorporated to store the control module 715 during the compression treatment. The compression device 750 shown in FIGS. 36-37 is configured to be wearable on a user's leg outside existing clothing. In this embodiment, individual segments 752, 753 are wrapped around the thigh and calf, respectively, and are connected by a segment 751. Each segment is initially held in position by straps 754 that are threaded through slots 755 in the panel 756. As shown in FIG. 36, the straps 754 may be integrated into a tensioning device 757 as described above. Each strap 754 may have hook-and-loop surfaces to either fasten back onto itself or fasten against the outer surface of the device 750, as shown in FIG. 37.

A further feature is the addition of a liner 753 that incorporates a cooling material, such as a cooling gel. The liner 753 may be pre-cooled, such as in the refrigerator, and then added to the device 750, such as by removable attachment or fitting within a pre-formed pocket, similar to the pouch 640 described above. Alternatively, the liner 753 may be a "nubbed" panel, namely a panel that includes relatively hard plastic nubs that bear against the skin. It can be appreciate that the liner 753 may be incorporated into all of the compression devices disclosed herein, whether configured with a cooling gel or as a "nubbed" panel or any other configuration adapted for therapeutic treatment. The control module 715 is connected to the compression assembly associated with the device 750 by a cable 703 and may be carried by a belt strap 756 configured to wrap around a waist belt.

Figure 38:
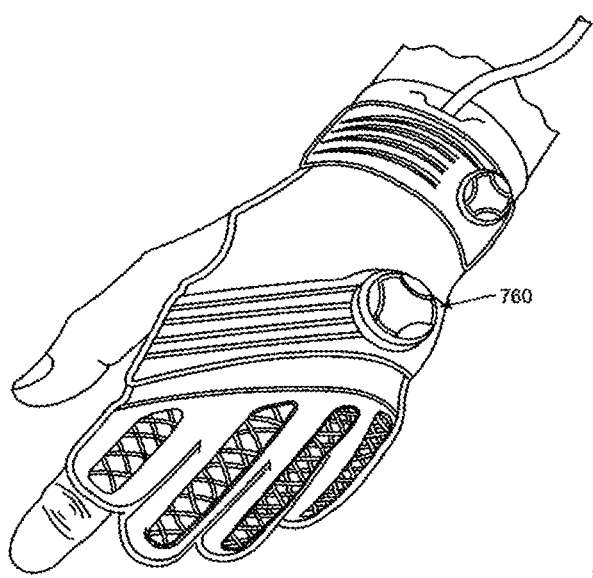
FIG. 38 is a perspective view of a wrist compression device according to the present disclosure.
Figure 39:
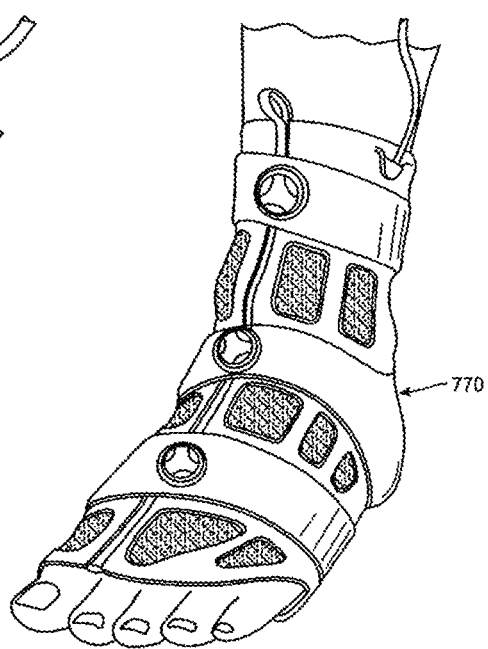
FIG. 39 is a perspective view of an ankle compression device according to the present disclosure
Figure 40A:
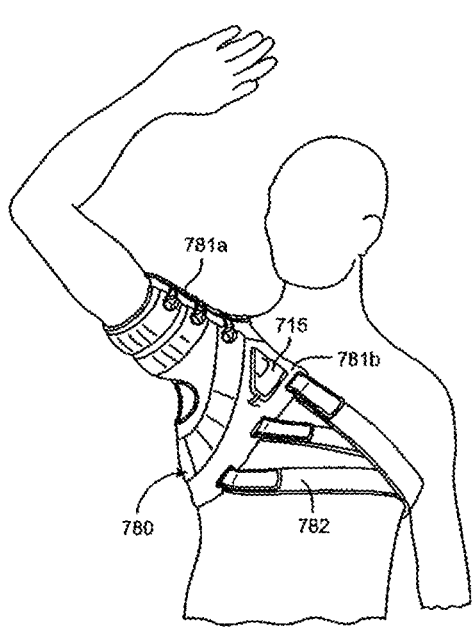
FIGS. 40a, 40b are perspective views of a shoulder compression device according to the present disclosure.
Figure 40B:
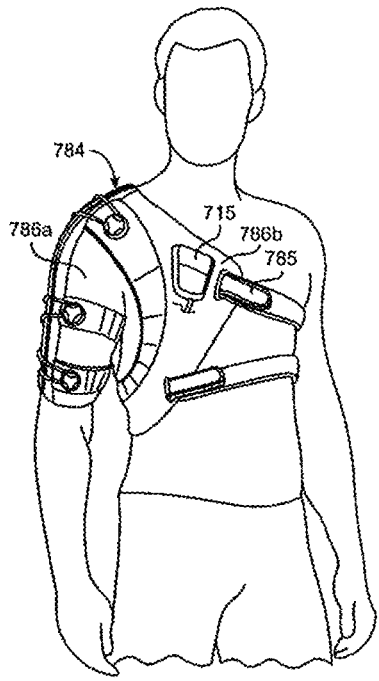
Figure 41:
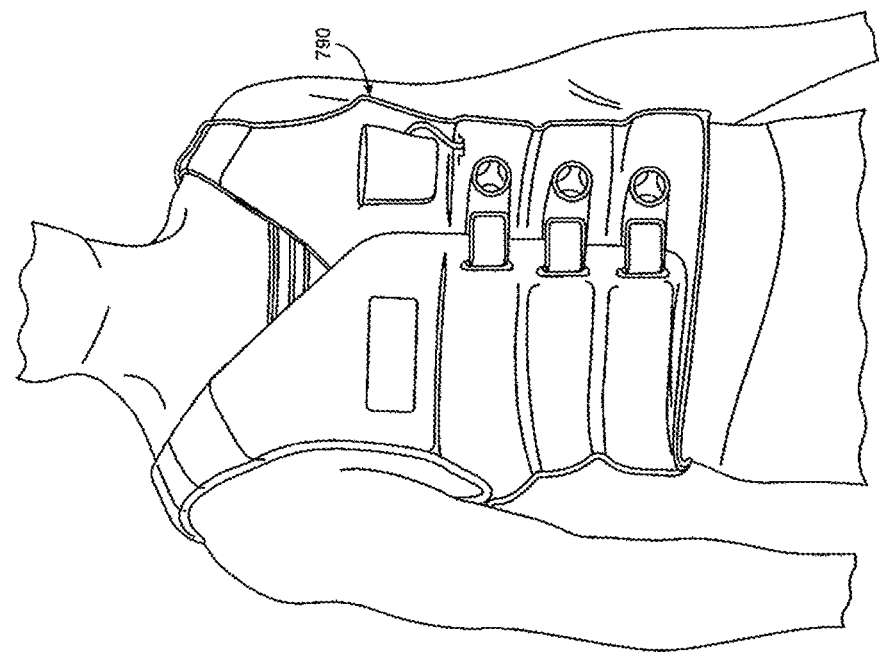
FIG. 41 is a perspective view of a torso compression device according to the present disclosure.

The compression devices described herein may be further modified to fit other parts of the body, such as the compression device 760 configured to be wrapped around the hand, and the device 770 configured as an ankle wrap, as shown in FIGS. 38, 39, respectively. A shoulder arrangement is shown in FIGS. 40a, 40b. The shoulder compression devices 780, 784 are configured to wrap around the upper arm and shoulder. The devices 780, 784 include a portion 781a, 786a that wraps around the upper arm and a portion 781b, 786b extends across the chest and upper back of the user. The devices are held in position by chest straps 782, 785, respectively, that extend from the portions 781b, 786b and wrap around the chest and back of the user. The devices may be provided with pockets for carrying the control module 715. A compression device 790 shown in FIG. 41 can be configured as a vest to be wrapped around the chest or torso of the user, particularly to apply compression to the back muscles. The vest can also be configured to apply compression to the front of the torso or completely around the torso as a part of a lung clearance therapy.

Figure 42:
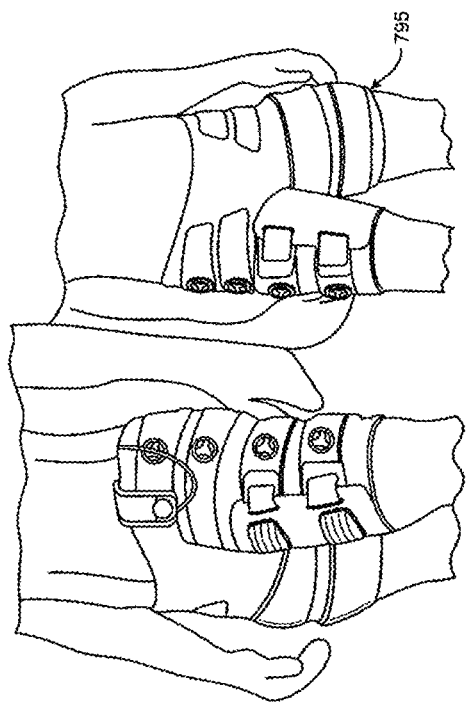
FIG. 42 are perspective views of a compression device adapted to treat the hip, IT band and gluteus muscles of the wearer according to the present disclosure.
Figure 43:
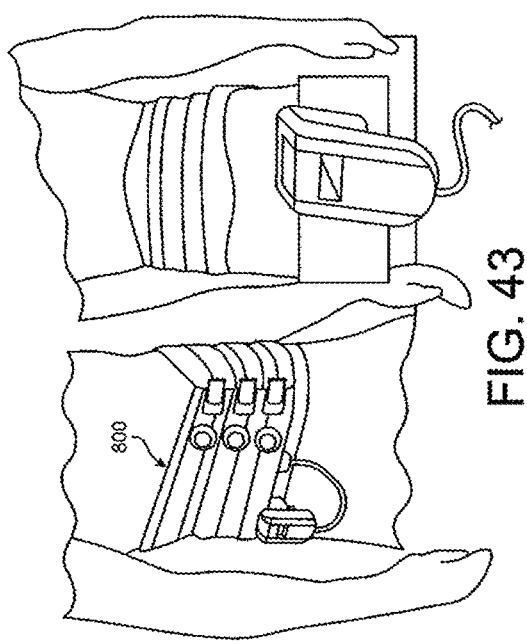
FIG. 43 are perspective views of a lumbar compression device according to the present disclosure.
Figure 44:
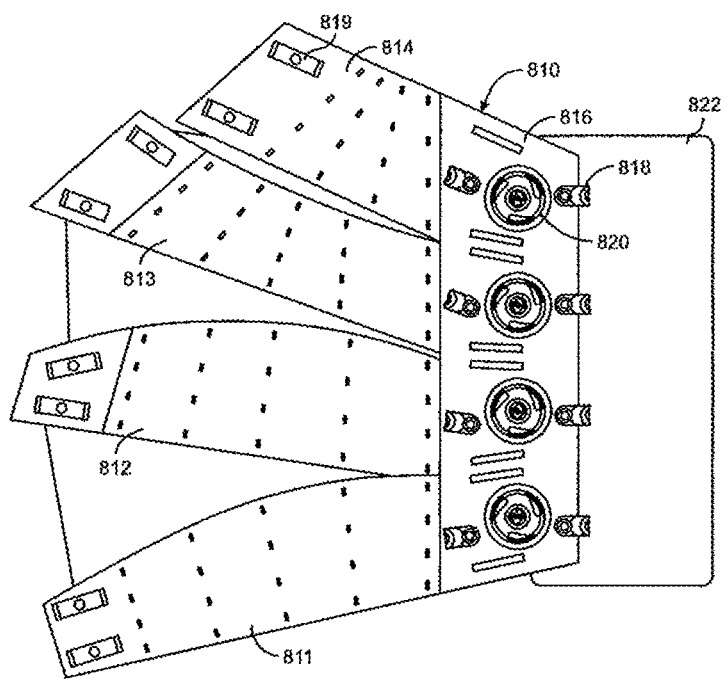
FIG. 44 is a plan view of a calf compression device according to the present disclosure.

The compression device 795 shown in FIG. 42 is configured to be worn like workout shorts to provide compression to the hip, IT band and gluteus muscles of the wearer. FIG. 43 shows a lumbar compression device 800 specifically configured to apply compression to the lower back. A calf compression device 810 shown in FIG. 44 includes multiple panels 811-814 extending from a base panel 816. Two of the panels 811, 812 are arranged to wrap around the lower calf of the user, while the panels 813, 814 are configured to be worn around the upper portion of the calf. The panels include quick-release connector components 818, 819 and a tension dial 820 similar to the connector and pre-tensioning components described above. A shield panel 822 may also be provided to overlap and cover the ends of the panels 811-814 when they are connected to the base panel around the calf of a user.

Figure 45A:
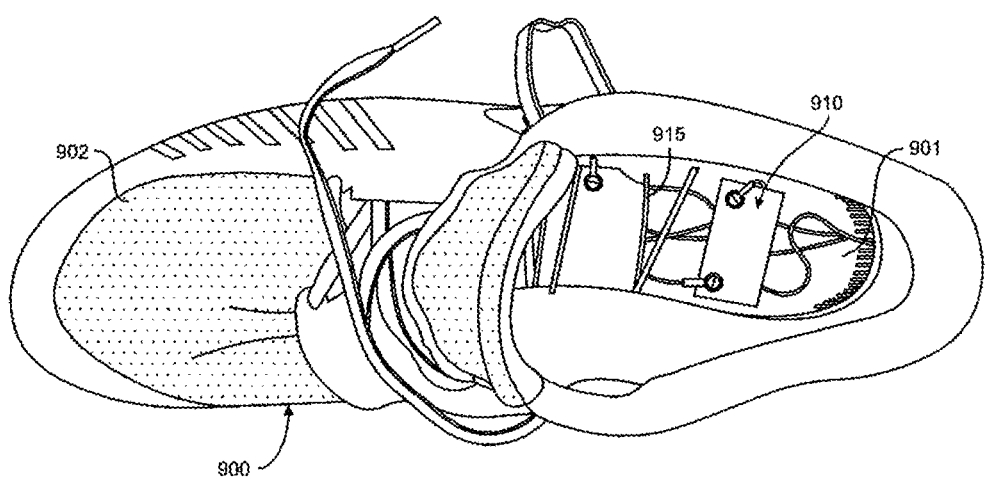

The compression device may be integrated into a shoe to provide compression or massage for the user's foot. Thus, as shown in FIGS. 45A-C, a show 900 with a sole 901 and an upper 902 includes a compression device 910 disposed between the sole 901 and the shoe insert (not shown). The compression device 910 includes SMA wires 915 that extend along the sole and along the inside of the shoe upper 902. A cap 920 is provided between the user's foot and the SMA wires 910 so that the wires are disposed between the shoe upper and the cap. The cap 920 is sufficiently rigid to protect the top of the user's foot from direct pressure from the SMA wires. The cap also helps distribute the compression force as the SMA wires are activated. The shoe insert protects the bottom of the user's foot. The compression device 910 can thus operate to apply a massage or compression protocol to the user's foot.

An alternative device 930 is shown in FIGS. 46A, 46B implemented within a shoe. The sole 932 of the shoe serves as an anchor for separate compression devices 935, 937 and houses the power and on-board control circuitry 940. The compression devices 935, 937 include corresponding SMA wires 936, 938 that are fed through loops 942 mounted to the shoe upper 934 in a generally sinusoidal pattern, as shown in FIGS. 46A, 46B. When the respective devices 935, 937 are activated the apply a compressive force C (FIG. 46B) at the center of the foot and at the Achilles tendon portion of the shoe to tighten the shoe on the user's foot. The power and control circuitry 940 may be activated by downward pressure by the user's heel on a switch embedded within the circuitry, or can be activated by an external switch. The external switch may be integrated into the sole 932 or the upper 934 of the shoe or may be part of a wireless component so that the device 930 can be selectively actuated by a smart phone. The SMA wires 936, 938 can be integrated into the material of the sole 932 and upper 934 to help insulate the SMA wire so that it does not lose heat too quickly, thereby allowing the SMA wire to hold its level of contraction with less power input to the wire.

Figures 46C, 46D:
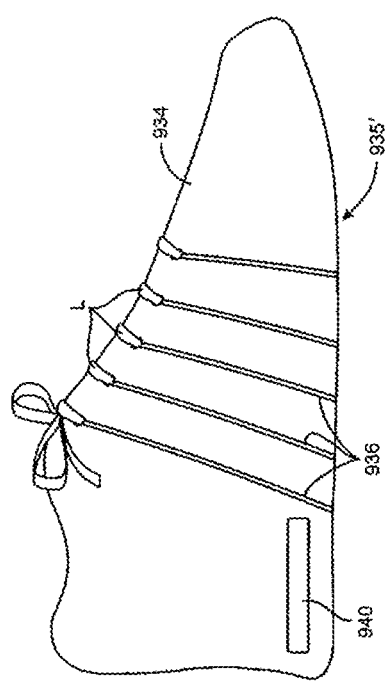
FIGS. 46c, 46d are side and bottom views of a shoe incorporating a compression device with an alternative configuration.

In a further modification, the compression device at the center of the shoe can be modified as shown in FIG. 46C. In particular, the compression device 935' can incorporate individual wires 936 that extend from the shoelace eyelets L and are embedded within the sole 932. The wires 936 are preferably placed within sheaths that are embedded within the sole 932 to allow the wires to contract within the sole of the shoe. The wires may also be embedded within the material of the shoe upper 934, also desirably within a sheath.

The compression devices disclosed herein incorporate a controller that controls the actuation of the SMA wires to apply the compression-release protocols described herein. The controllers for the compression devices may incorporate a microcontroller, such as microcontrollers 24 or 66 described above, that controls the duty cycle of the current applied to each of the SMA wires of the particular device. The microcontrollers may incorporate pulse-width modulation techniques to control the actuation time of the SMA wires to protect from overheating the wires. By way of example, the microcontrollers are configured to apply current to an actuated SMA wire long enough to achieve a 2-15% reduction in length or shrinkage of the wire over a predetermined time period. In specific examples, a voltage of 5-30V and a current of 0.2-4 amps is applied for a duration of 1.5-3.5 seconds. The duty cycles can vary between 35-100%. The PWM frequencies can be in the range of 2-10 kHz. This controlled actuation applies the desired compression for a time period that provides a desirable compression sequence for the user without generating too much heat. The sequence in which successive SMA wires are actuated can be used to provide sufficient time for a wire to cool down before being actuated again. Since the actuation properties of the SMA wire are a function of the length and diameter of the wires, the microcontroller can be provided with MOSFET switches corresponding to certain predetermined wire lengths/diameters.

The present disclosure contemplates compression devices that are worn on the body of a person. This application of SMA wires involves certain challenges to providing uniform, controllable contraction of the device while also preventing electrical shock and over-heating of the user, and while further doing so in an energy efficient manner. In accordance with the devices disclosed herein, it is contemplated that a power source in the range of 5-50 watts can be required to produce effective results for large scale compression. This power requirement can be satisfied by a 12 volt power supply, whether by the use of on-board high-energy batteries, such as lithium polymer batteries, or by the use of an electrical adapter/transformer connected to a separate electrical source.

A further complexity is providing a useful combination of force and stroke with the an SMA wire device. A typical SMA wire, such as a Nitinol wire, can contract about 4% of its length when heated. Thus, simply winding a single SMA wire around a body part, such as a thigh, does not provide sufficient compression for most purposes. For instance, it has been found that an 8-10% decrease in the diameter of a large muscle, such as the thigh, is necessary for an optimum "feel" and effectiveness. Moreover, the compression force needs to be distributed over a larger area in order to avoid the single wire "garroting" effect. Greater force distribution militates in favor of a larger diameter SMA wire, which can provide greater compressive forces but at the cost of greater energy input requirements.

Another factor in the complexity of an SMA-based wearable compression device is the speed of the contraction. In some applications of the present compression device, a therapeutic compression can be achieved with a rolling two second compression wave. The resultant energy expenditure of this compression wave leads to waste heat that must be removed or the device can worm up to levels that are uncomfortable to the user. Thus, the present device contemplates a combination of energy management, thermal insulation and activation cycle time to optimize the speed of contraction and its effects on the user.

Since a single SMA wire is generally inadequate to provide sufficient compression for meaningful utility, some sort of stroke amplification is required. The devices disclosed above provide one mechanism for stroke amplification, such as the devices shown in FIGS. 9-25. Further approaches are disclosed below.

Figure 47:
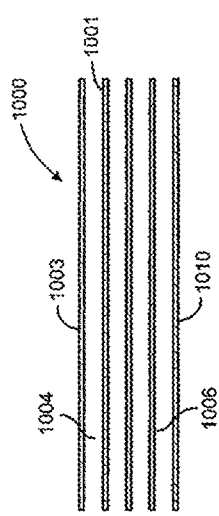
FIG. 47 is a side representation of an SMA wire according to one aspect of the disclosure in which the wire is embedded within a sheath.

The devices disclosed herein can incorporate an SMA wire that is coated or encapsulated in an elastomeric material. Thus, in one embodiment shown in the diagram of FIG. 47, a wire arrangement 1000 includes an SMA wire 1001, which can be similar to the SMA wires discussed above, that is shrouded within an elastomeric sheath 1003. In one embodiment, the sheath 1003 can be formed of a silicone or polyurethane material. In one embodiment, the sheath 1003 may be formed directly on or coated onto the SMA wire 1001. The elastic nature of the sheath material allows the sheath to expand and contract with the SMA wire. The sheath may have a thickness calibrated to provide a larger diameter for the wire arrangement 1000 than the SMA wire 1001 itself. This larger overall diameter helps distribute the force produced by the wire arrangement when the SMA wire is contracted. Alternatively, a gap 1004 may exist between the sheath 1003 and the SMA wire 1001 so that the wire can slide independent of the sheath. The gap 1004 provides an additional level of insulation beyond the thickness of the sheath itself. On the other hand, the gap 1004 is not necessary for actuation of the wire arrangement and can lead to bunching of the sheath when the compression device is activated.

The material of the sheath 1003 is adapted to have a thermal conductivity sufficient to help the SMA wire 1001 maintain its temperature upon contraction with only limited additional energy input required to maintain the same level of compression. The thermal mass and specific heat capacity of the sheath can be calibrated by changing the thickness of the coating material applied to the SMA wire. In addition, the basic sheath material can be doped with a thermally conductive or thermally insulative material to adjust the overall conductivity of the sheath. For instance, the sheath 1003 may be infused with air bubbles or may incorporate glass beads or diamond dust. The sheath 1003 may selectively incorporate insulative components immediately adjacent the body 1010 of the underlying fabric that contacts the user's skin, and may selectively incorporate thermally conductive components on the outer surface. The SMA wires are, in effect, resistive heaters so the temperature increase of the SMA wires is known if the voltage pulse durations to the wires is known. The thermal conductivity, diffusivity and thermal mass of the sheath regulates the thermal energy leaving the wire arrangement 1000 as well as the heat experienced by the user wearing the compression device.

Figures 48A, 48B:
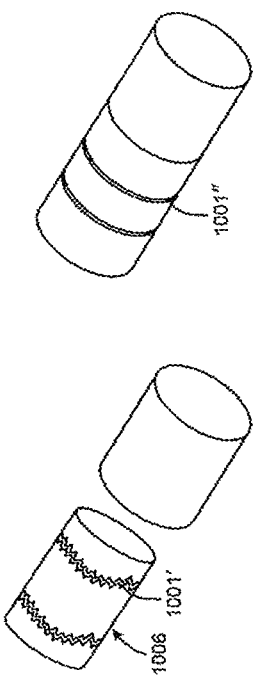
FIGS. 48a, 48b are presentations of a compression device incorporating a sinusoidally wound SMA wire with the wire depicted in its relaxed and stretched states.

Returning to FIG. 47, a further benefit of the sheath 1003 is depicted. In particular, the sheath can facilitate attachment of the wire arrangement 1000 to the body of the compression device. In one embodiment, the sheath 1003 may be affixed to an elastic fabric 1006 of the compression device. The fabric 1006 may be formed of a material capable of spreading the compression forces that are generated by contraction of the SMA wire. Thus, the fabric may be a bamboo or nylon material that can be curved to fit the shape of the user's body. In a further aspect the SMA wire 1001' of compression device 1010' may be formed in an initial sinusoidal configuration, as depicted in FIG. 48Aa. The sinusoidal configuration allows the SMA wire 1001' to act like a spring. The wire can then readily stretch or straighten as the fabric 1006 stretches. Thus, as the device is mounted on the body of the user, the fabric 1006 of the device stretches and the SMA wires 1001" become substantially straightened, as depicted in FIG. 48B. This straightening of the SMA wires serves to apply a pre-tension to the wires. When the SMA wires 1001" are energized they attempt to return to their original sinusoidal shape, thereby applying compression to the user's body.

Figure 49B:
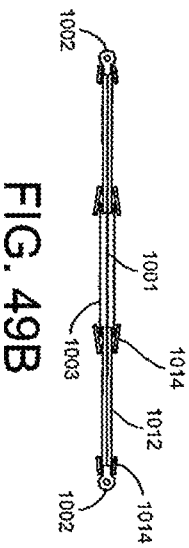
FIGS. 49a, 49b are top and side representation of an SMA wire within a sheath with an anchor feature according to a further aspect of the present disclosure.
Figure 49A:
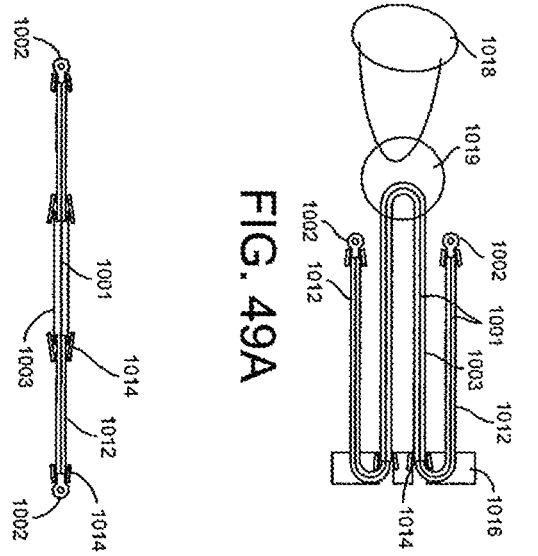

In a further embodiment, the SMA wire 1001 and silicone sheath 1003 can be incorporated into an arrangement that incorporates a second sheath 1012, as shown in FIGS. 49A, 49B. As shown in FIG. 49A, the silicone sheath 1003 is formed into a U-shape, with one end anchored to an anchor piece 1019 for connection to an adjustable closure 1018, which can be similar to the closure 706 shown in FIG. 34A. The SMA wire 1001 is anchored to an underlying fabric layer, such as fabric 1006 in FIG. 47, by anchors 1002. The silicone sheath 1003 is affixed to a less pliant tubing, such as nylon tubing 1012, by fittings 1014. The fittings 1014 may be in the form of shrink tubing that is heat shrunk around both tubings 1003, 1012 to secure fix the tubing together. The fittings 1014 may be fastened to a separate anchor strip 1016 that is fastened to the underlying fabric. The same fitting can be used to affix the nylon tubing to the SMA wire anchors 1002, as shown in FIG. 49B. The nylon tubing has a low friction inner surface but is otherwise generally less pliant than the silicone tubing 1003. This combination of tubing focuses the stroke of the compression device to the silicone tubing 1003, thereby providing a well-controlled region of compression.

The voltage duty cycle can be regulated to regulate not only the energy entering the system but also the energy leaving the system. Reducing the thickness of the sheath 1003 increase the thermal energy expelled from the wire arrangements 1000, which thermal energy manifests in an increase in temperature of the compression device to the user, which may be desirable. Alternatively, increasing the thickness of the sheath 1003 decreases the thermal energy exiting the wire arrangement so that the compression device no longer performs like a heating pad. However, limiting the thermal energy leaving the wire arrangement means that more heat is retained by the SMA wire, which in turn means that less additional energy is required to keep the SMA wire arrangement at its level of contraction.

In some cases it is desirable to cycle the wire arrangement between the contracted condition (i.e., Austenitic phase of the SMA wire) and the relaxed condition (i.e., Martinsitic phase of the SMA wire). In this case a balance must be maintained between the input energy and the thermal energy that is either stored/retained by the sheath and the energy that is dissipated through the sheath. In this case, shorter input pulses of higher voltages may be preferred, with the understanding that the higher input voltages produces faster actuation speeds for the device. Tight control can be achieved by monitoring the current in the SMA wire 1001. For example, a Nitinol wire of 50 inch length and 0.015 inch diameter in a silicone sheath pressed against the body can require 21 volts to heat the wire to full phase change in about 2.5 seconds. The initial current pulse is about 1.7 amps and then peaks to about 2 amps after the phase change. If there is a positive heat transfer from the wire arrangement to the body a steady state condition can be achieved in which the energy applied to the wire arrangement equals the energy exiting. When the current can be increased no further, the wire temperature can be maintained at just above the Austenitic state nearly indefinitely. On the other hand, if the heat transfer is negative, meaning that heat is transferred from the person's body to the wire arrangement, the wire temperature can rise quickly once the SMA wire reaches its Austenitic phase. It is at this point that the controller can turn off the voltage applied to the wire arrangement to regulate both the contraction of the wire arrangement and the heat transfer condition between the user and the wire arrangement. In addition, at this point the voltage may continue to be applied to the wire arrangement in order to achieve a particular heating effect during a compression cycle, being careful to avoid overheating the SMA wire. In a typical case the SMA wire can be damaged if its temperature exceeds 130° C.

In accordance with one aspect of the present device, the device controller monitors the current flow through the SMA wires, and in particular monitors the change in slope of the current pulse. If the slope falls below a threshold the electrical current is shut off to the SMA wire. In one example, that threshold is when the slope drops below 0.1 amp per second increase. The current can be measured by Hall-effect sensors or similar means, and the slope can be calculated in real-time by the controller and stored throughout each actuation cycle for continuous evaluation. As a fail-safe, a maximum voltage pulse on-time can be established, such as 2.5 seconds for a given actuation cycle. It is contemplated that the actuation time for a compression device according to the present disclosure may require a longer cycle time when the device is first turned on because the SMA wires are at ambient temperature well below the phase transition temperature. It is further contemplated that with each successive actuation cycle the actuation time will decrease because the SMA wire has already reached the transition temperature and the ability of the sheath to shed thermal energy gradually decreases as the user's body temperature inside the compression device increases. Under these conditions it is then necessary to shorten the voltage pulses to prevent the SMA wire from over-heating. Under certain conditions, extended "rest" for the compression device and wire arrangements may be necessary to allow the SMA to cool below the transition temperature and below the Martinsitic finish temperature. Thus, in some cases this rest period can be 60-90 seconds.

Figure 50:
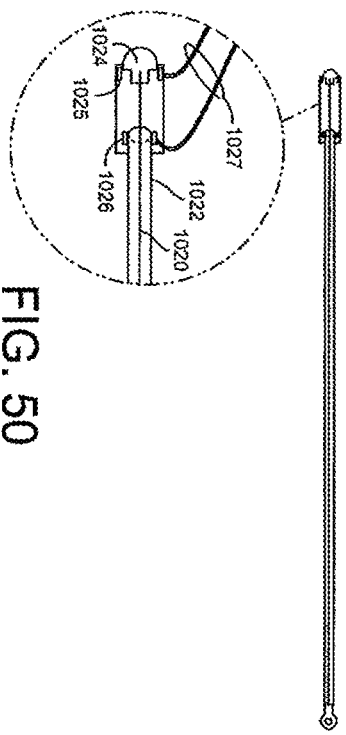
FIG. 50 is a side and enlarged view of an anchor feature according to a further aspect of the disclosure.

In one method for controlling the current flow through the SMA wires, the length of the wires can be continuously sampled and then the current shut off to the wires when they reach their fully transformed length. Thus, in one aspect, a time domain reflectometer (TDR) or a frequency domain reflectometer (FDR) can be used to measure the initial length of the SMA wire and then to continuously sample the wire length. The TDR or FDR can be configured to signal the device controller to turn the power off when the wire shrinks to its full transformation length. In another approach, a mechanical switch may be provided in lieu of the TDR or FDR. Thus, as shown in FIG. 50, the SMA wire 1020 may be anchored to an end connector 1024 and slidably disposed within a sheath 1022. Electrical contacts 1025 are mounted to the end connector 1024, and contacts 1026 are mounted to the end of the sheath 1022, with wires 1027 communicating with the device controller. When the SMA wire 1020 shrinks to its desired length, the contracting wire draws the end connector 1024 toward the sheath 1022 until the electrical contacts 1025, 1026 meet. When the contacts meet, the wire circuit 1027 is closed to send a signal to the device controller which responds accordingly to stop current flow to the SMA wire 1020.

Figure 51:
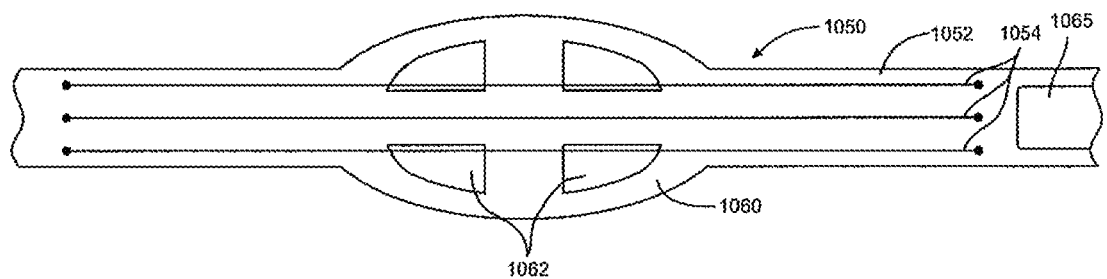
FIG. 51 is a top view of compression device incorporating an electrical stimulation component according to one embodiment of the present disclosure.

In a further embodiment, a compression device 1050 combines the active compression features of the SMA wire devices described above with an electrical stimulation device. Thus, as shown in FIG. 51, a compression device 1050 can include a base 1052 configured to be worn on the user, such as in the manner of any of the compression devices described herein. The device is provided with SMA wires 1054 that are powered and controlled by a device controller 1065, again in any of the manners described herein. The base 1052 includes a stimulation region 1060 on which is mounted a plurality of electrical stimulation devices 1062. In one embodiment, the devices are TENS—transcutaneous electrical nerve stimulation—units. The TENS units 1062 are connected to the device controller 1065 which is configured to activate and control the TENS units according to a desired protocol, such as by controlling pulse width, frequency and intensity of the electrical signal emanating from the devices. The compression device 1050 can position at least one SMA wire 1054 over each TENS unit 1062 to help press and maintain the TENS unit in direct contact with the user's skin, which is necessary for the TENS units to operate. Since the SMA wire electrical requirements and duty cycle may differ from the TENS unit duty cycle and electrical requirements, the TENS units 1062 are separately wired to the device controller 1065.

The device controller 1065 can be configured to modulate the SMA wires and TENS units according to a desired protocol. For instance, in one protocol the SMA wires 1054 are activated to provide compression for a fixed period, say four seconds, and then while the SMA wires are relaxed the TENS units 1062 are activated for another four seconds, followed by four seconds of rest. This cycle can be repeated as long as desired, and may be accompanied by the addition of heat to the compression and/or TENS activation parts of the cycle.

Figure 53:
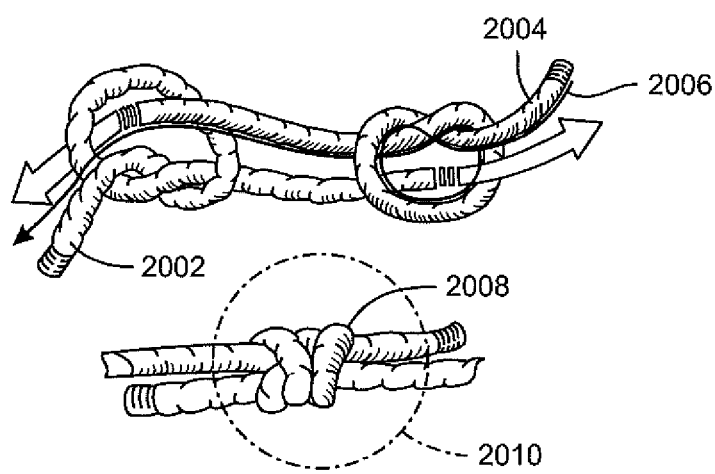
FIG. 53 is an enlarged view of the connection between the pre-tensioning element and the SMA wire and electrical wires shown in FIG. 52.
Figures 54A, 54B:
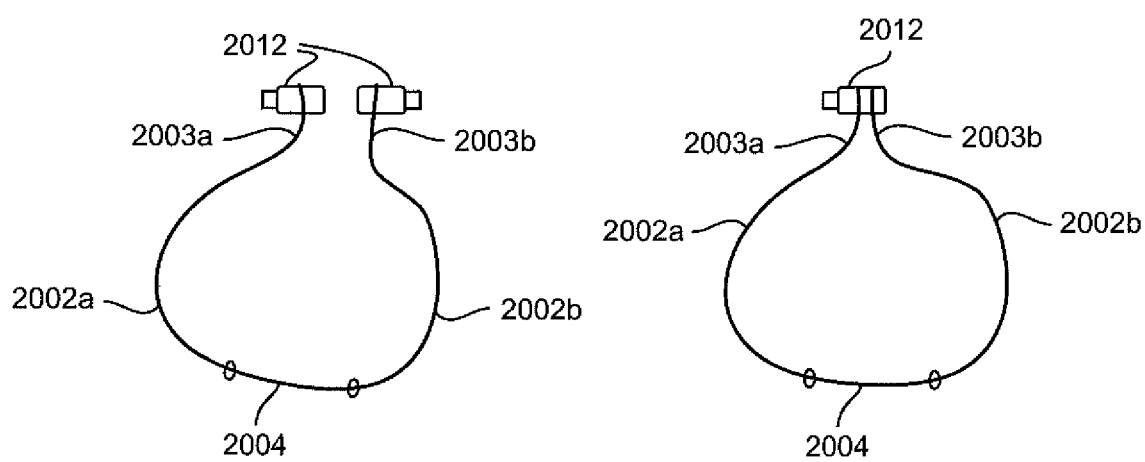
FIGS. 54A, 54B are schematic representations of the compression engine of FIGS. 52-53 with different clamps for the pre-tensioning element.

In the previous embodiments of the compression device, the SMA wires can be pre-tensioned using a mechanical element, such as the tension dial component 711 shown in FIGS. 34a-34B. In an alternative embodiment, the compression engine includes an elastic pre-tensioning element connected to the SMA wire. Thus, a compression engine 2000 shown in FIGS. 52-53 includes an elastic pre-tensioning element 2002, which may be a bungee cord in one specific embodiment. Although not depicted in the figure, the elastic element, or bungee cord, is sized to encircle the body portion of the wearer and is further sized to apply a known compression to the body portion when the compression device is worn. In one embodiment, the bungee cord is continuous, or may be discontinuous as illustrated in FIGS. 54A-54B. In the discontinuous embodiments, two bungee cords 2002a, 2002b are connected to the SMA wire 2004. The pre-tensioning element is connected to the SMA wire 2004 at locations 2008. In one aspect, the connections are in the form of a "fisherman's knot", as illustrated in FIG. 53, so that the knot, and therefore the connection, tightens as tension is applied to the bungee cord 2002 and/or the SMA wire 2004. The connection 2008 can be shrouded in a suitable material or fabric to prevent contact with the connection of the electrical wires to the SMA wire.

Figure 52:
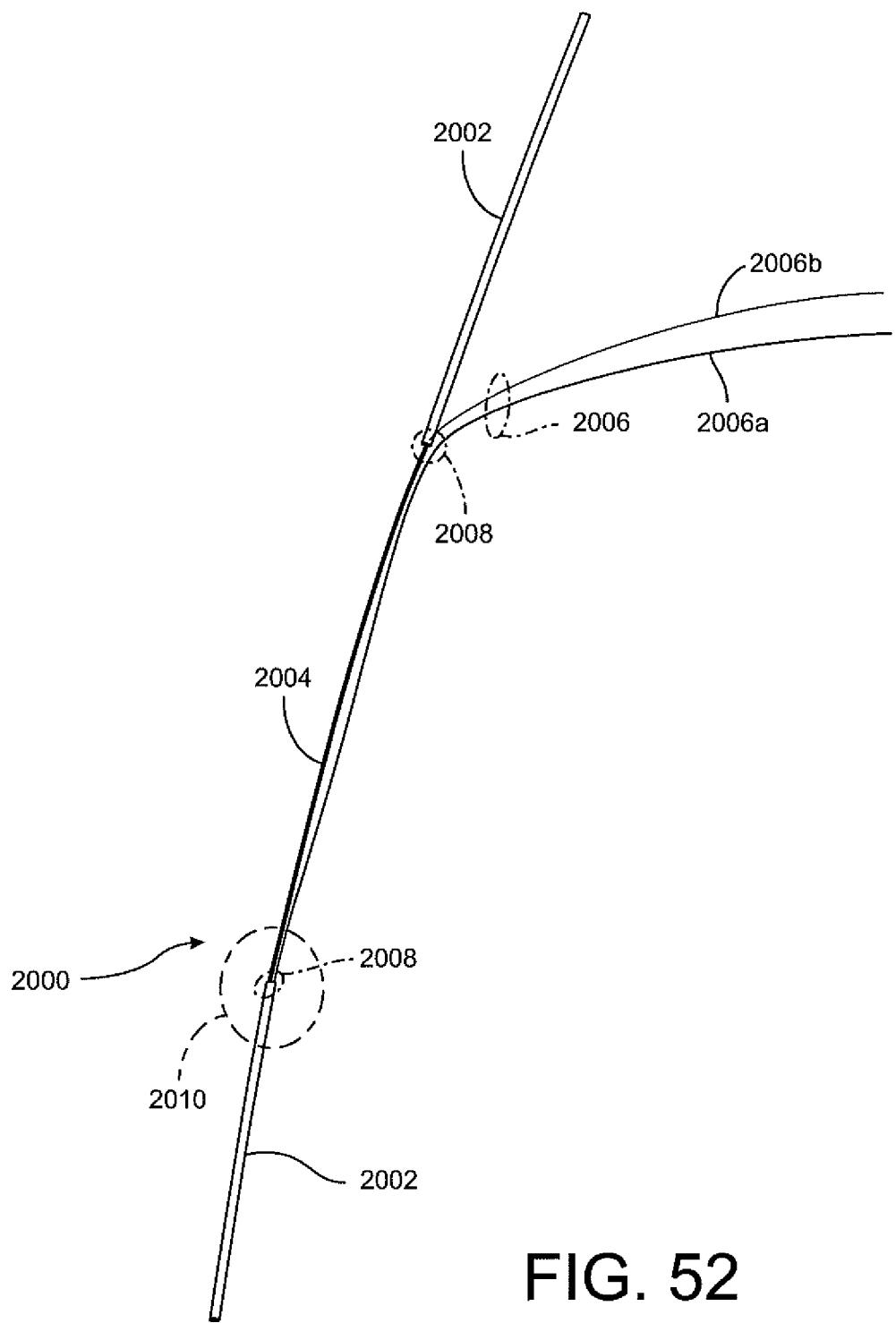
FIG. 52 is a depiction of a compression engine according to a further aspect of the present disclosure including a pre-tensioning element connected to an SMA wire and electrical wires according to one embodiment of the compression device disclosed herein.

Although not depicted in FIG. 52, the elastic element, or bungee cord, can be sized to encircle the body portion of the wearer. In this embodiment, the SMA wire 2004 is contiguous with the bungee cord along the length of the SMA wire, with the ends of the SMA wire connected to the continuous bungee cord by the "fisherman's knots". In another embodiment, the pre-tensioning element includes two bungee cord segments 2002a, 2002b, each connected at one end to the SMA wire 2004, as depicted in FIGS. 54A, 54B. In these embodiments, the free ends 2003a, 2003b are engaged by one or more bungee clamps 2012. In the version shown in FIG. 54A, each end 2003a, 2003b is engaged by its own clamp 2012, which allows for individual adjustment of the tensioned length of the corresponding bungee cord segment. In the version shown in FIG. 54B, the two free ends 2003a, 2003b are engaged by a single clamp. The clamps 2012 can be known barrel-style cord locks or other adjustable clamping elements suitable for solid clamping of cord ends.

Figure 55A:
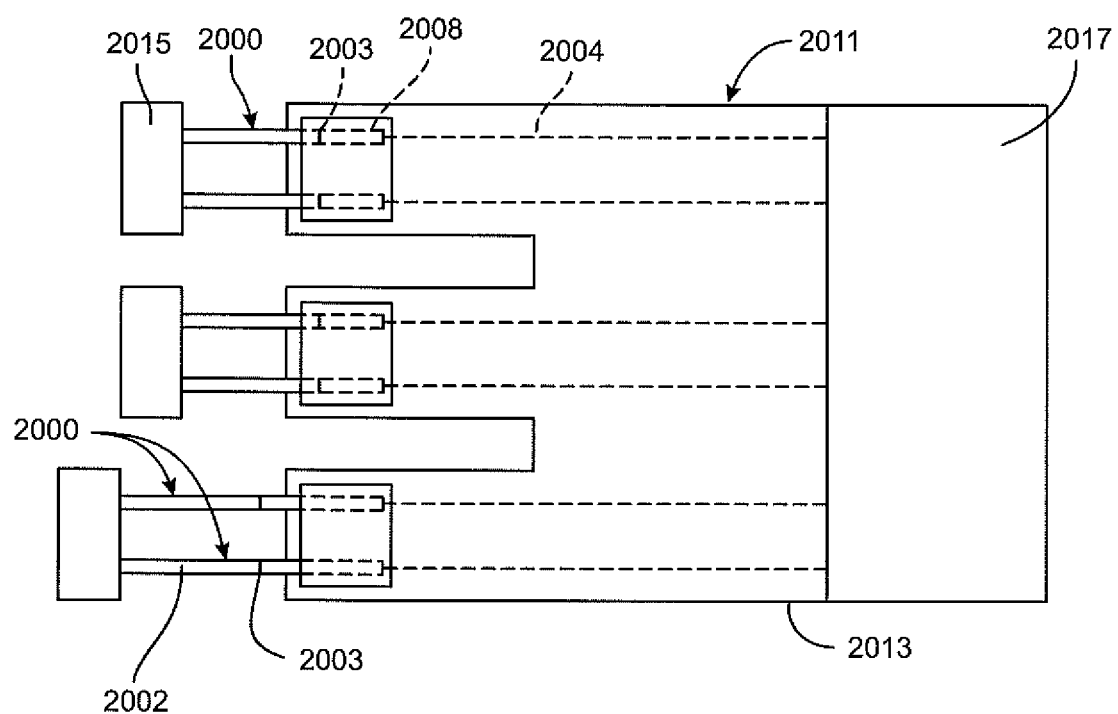
FIG. 55A is a plan view of a compression device incorporating the compression engine of FIGS. 52-53 with pre-tension markings on the pre-tensioning element of the compression engine.
Figure 55B:
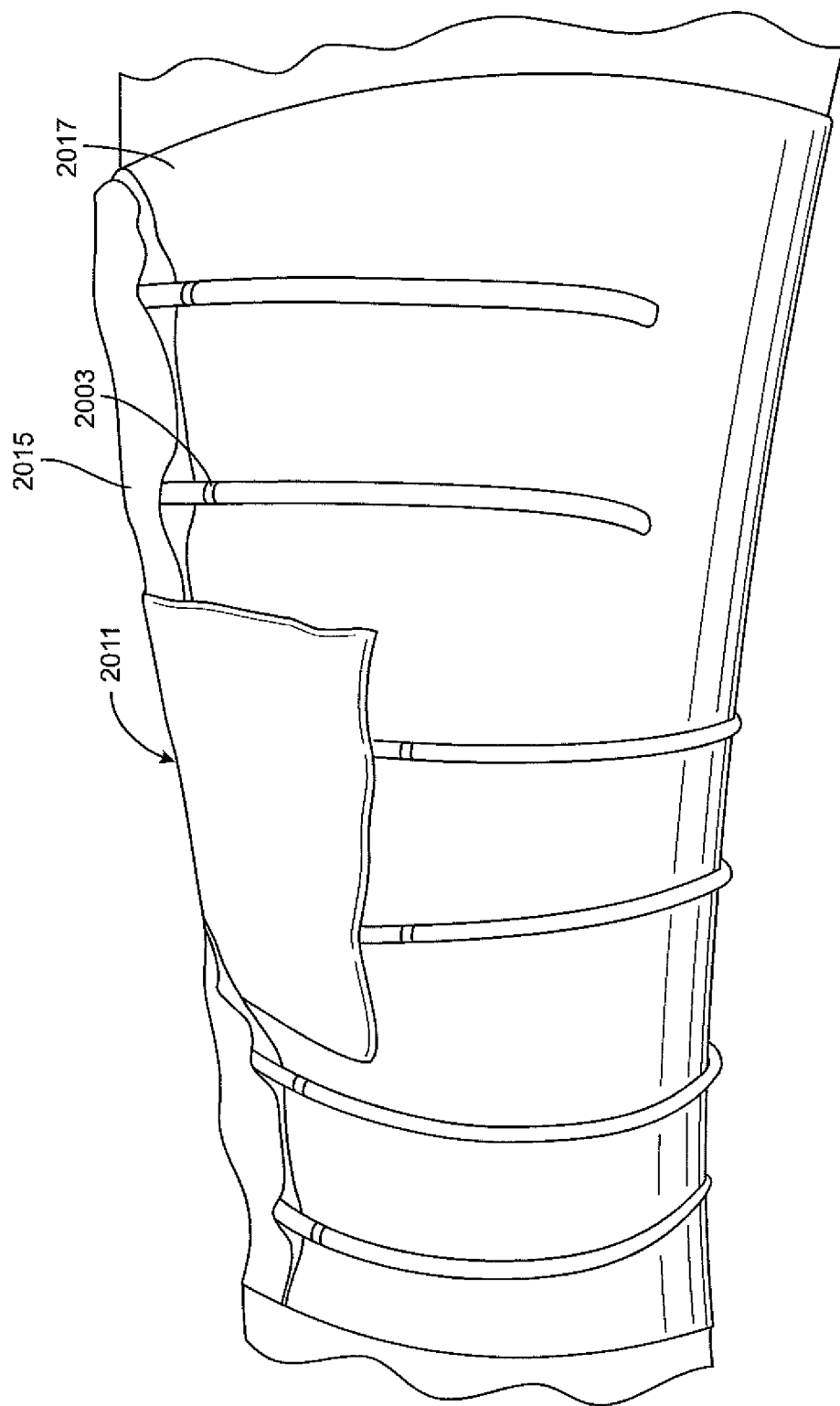
FIG. 55B is a perspective view of the compression device shown in FIG. 54A wrapped around the leg of a wearer.

The compression engine 2000 shown in FIGS. 52-53, 54A-54B can be incorporated into a compression device 2011 shown in FIGS. 55A, 55B. The device in this embodiment is similar to the compression device shown in FIG. 44 in that it is a calf compression device, although the principle of this embodiment can be incorporated into other of the compression devices disclosed herein. The compression device 2011 includes a fastener strip 2015 associated with each of the compression engines 2000 in which the fastener strip engages a fastening region 2017 of the body 2013 of the compression device. The device is thus sized to encircle the calf of the wearer (or other body portion for others of the compression devices), with the fastener strips 2015 releasably engaged to the fastening region. The fastener strips and fastener region can incorporate hook and loop fasteners that can be firmly engaged and readily disengaged.

The free end of each pre-tensioning element or bungee cord 2002 of each compression engine 2000 is affixed to a corresponding fastener strip 2015. As shown in FIG. 55A, the connection 2008 between the pre-tensioning elastic element 2002 and the associated SMA wire 2004 is contained within the body 2013 of the compression device, with the end of the elastic element 2002 extending out from the end of the body 2013. When the compression device is worn, each elastic element 2002 is stretched so that the associated fastening strip 2015 can be engaged to the fastening region 2017. This stretch of the elastic element 2002 applies a pre-tension to the compression engine 2000, as discussed above. In order to ensure a proper amount of pre-tension, the elastic element or bungee cord 2002 is provided with a marker 2003 that is initially concealed within the body 2013 of the device 2011 when the elastic element is in its free state. The marker 2003 becomes visible outside the body 2013. When the marker 2003 is visible the wearer of the device knows that the pre-tensioning elastic element 2002, and therefore the associated compression engine 2000, is properly pre-tensioned. The location of the marker 2003 on the elastic element 2002 is calibrated so that the marker remains hidden unless and until the elastic element has been stretched a pre-determined amount, corresponding to the desired pre-tension. The location of the marker 2003 is thus also calibrated so that it becomes visible at the appropriate amount of stretch. Alternatively, the marker 2003 can be calibrated to be aligned with another indicia on the body 2013 of the compression device, again indicative of the proper amount of stretch and pre-tension.

Since the elastic element 2002 is connected to the SMA wire 2004, it is important that the elastic element not be stretched too much because once the elastic element reaches its stretch limit further tension on the compression engine 2000 only attempts to stretch the SMA wire 2004. The marker 2003 is thus calibrated so that the wearer will not over-stretch the compression engine, thereby impeding its proper function.

In one embodiment, the elastic element 2002 can include a marker 2003 in the form of a line or band on the elastic element. Alternatively, the marker 2003 can be the delineation between differently colored portions of the elastic element or bungee cord. For instance, the portion of the bungee cord that is visible in the free state of the cord can be blue, but the portion of the bungee cord beyond the marker 2003 can be red to provide a clear visual indication of the appropriate amount of stretch to the bungee cord. Thus, as the wearer engages each attachment strip 2015 to the attachment region 2017, he/she simply stretches the compression engine 2000 until the marker 2003 is visible, and then engages the attachment strip to the attachment region.

Figure 56A:
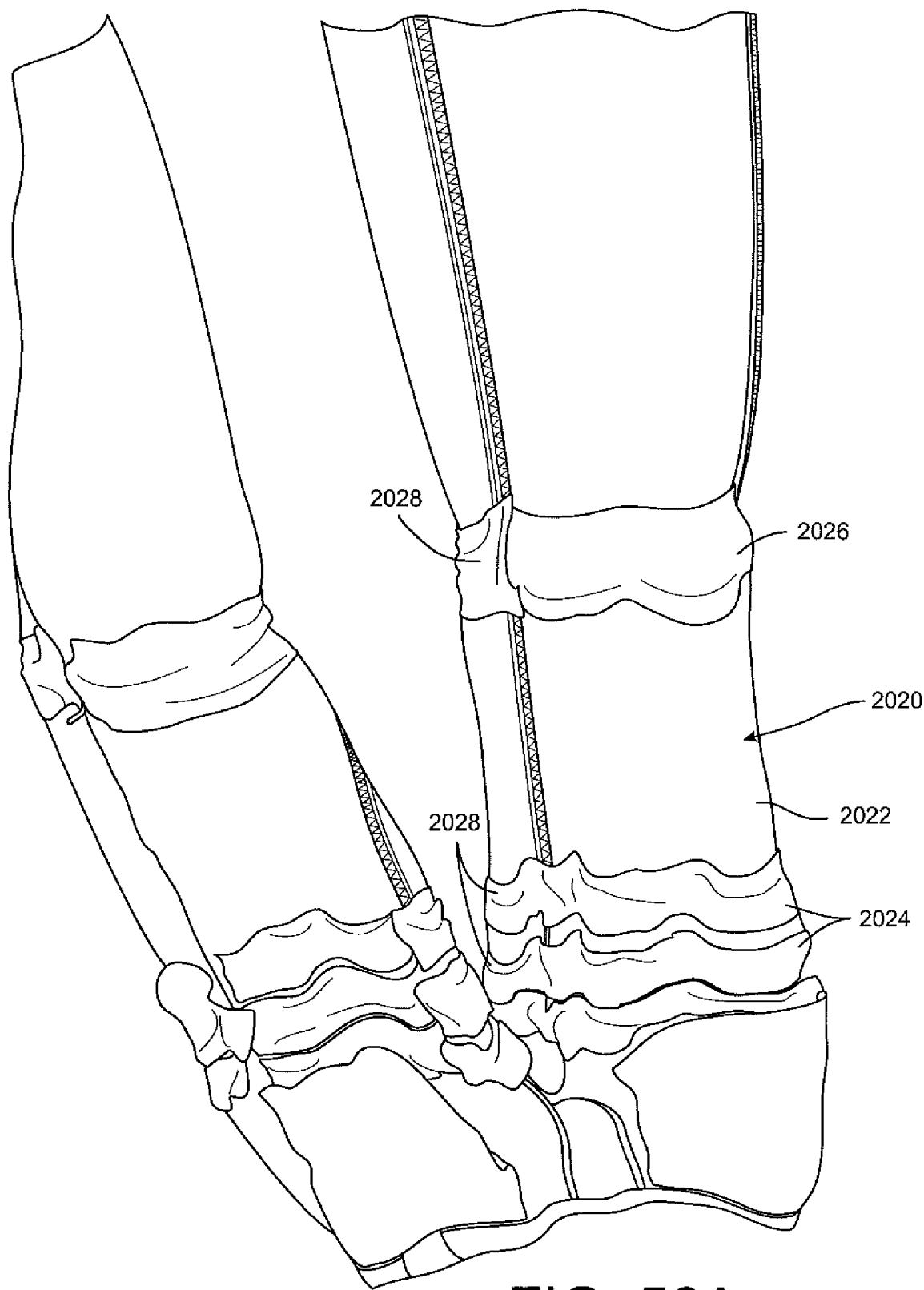
FIG. 56A is a view of the interior of trousers incorporating the compression engine of FIGS. 52-53.
Figure 56B:
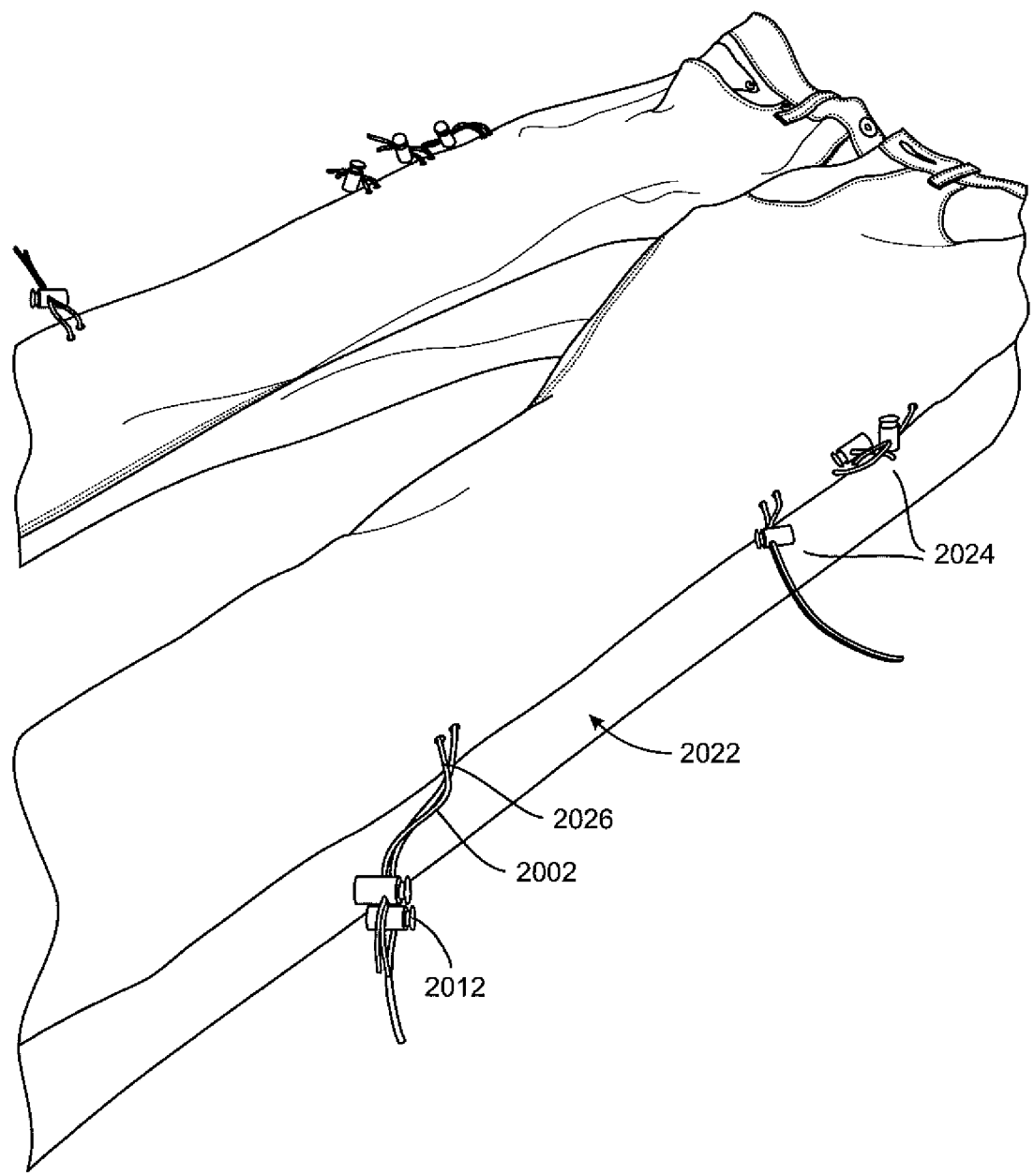
FIG. 56B is a view of the exterior of the trousers shown in FIG. 54A.

The compression engine 2000 can be incorporated into various articles of clothing. In one example, each leg 2002 of trousers 2020 can incorporate multiple compression engines, with two engines 2024 at the thigh location and one or more engines 2026 at the upper portion of the lower leg, as depicted in FIGS. 56A, 56B. As shown in FIG. 56A, the SMA wire and elastic element of the engines 2024, 2026, are covered with a cloth strip 2028 to protect the wearer's leg. As shown in FIG. 56B, the bungee cords 2002 of the compression engine are sized so that the free ends of the cords extend outside the article of clothing and include clamps 2012 engaging the free ends to permit adjustment of the initial tension provided by the bungee cord. The compression engine can be configured with the elastic element, or bungee cord, 2002 being co-extensive with the corresponding SMA wire 2004, with the two components 2002, 2004 connected in a middle portion of the components. Alternatively, the SMA wire can have a limited length and is connected end-to-end with two elastic elements in the manner shown in FIG. 52. In this alternative, the combined length of the SMA wire and the two elastic elements is sized to encircle the trousers or the leg of the wearer. In both cases, the free ends of the elastic element can extend outside the trousers for engagement by the clamp(s) 2012.

Figure 57A:
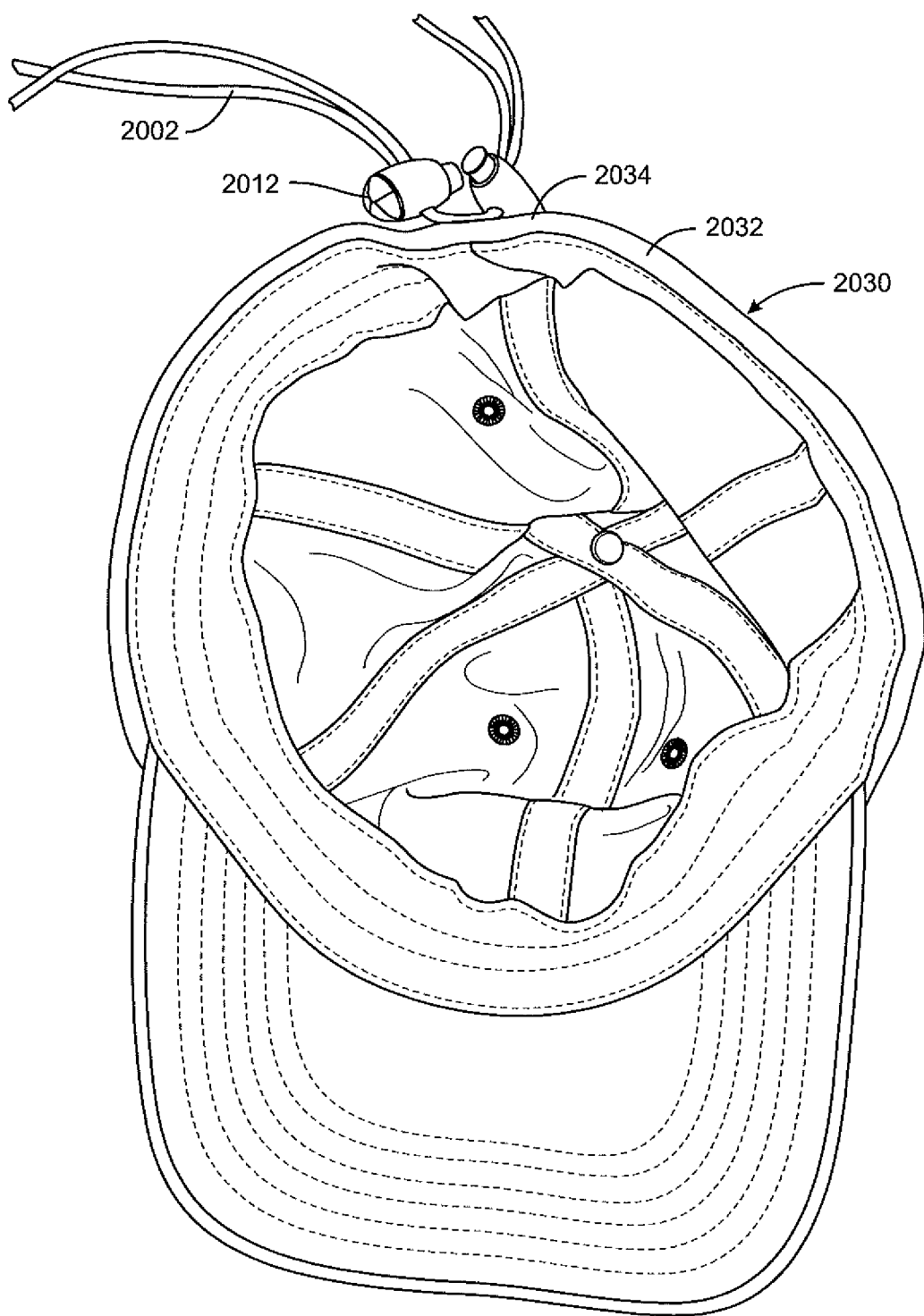
FIG. 57A is a view of the interior of a hat incorporating the compression engine of FIGS. 52-53.
Figure 57B:
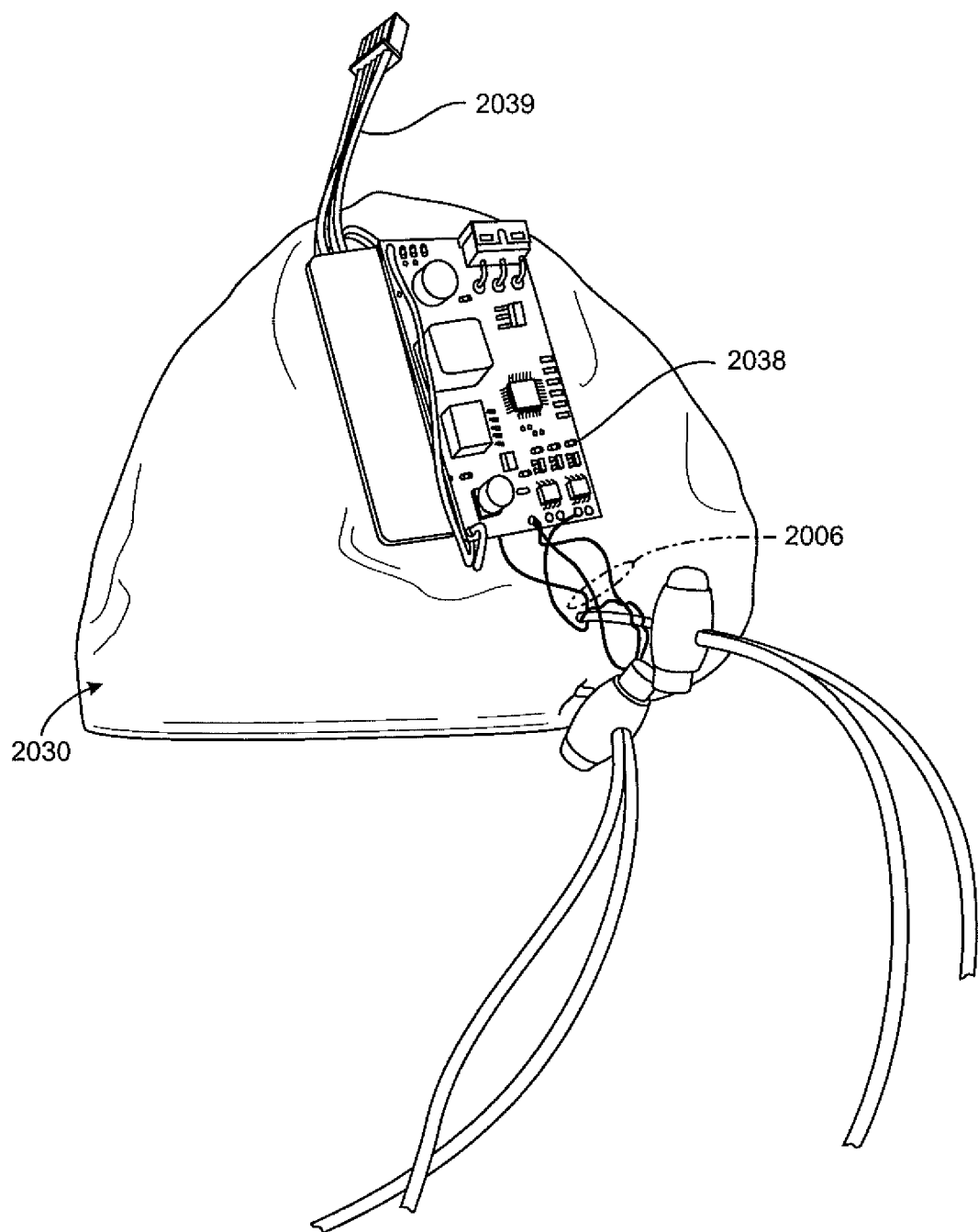
FIG. 57B is a view of the exterior of the hat shown in FIG. 54A.

The compression engine 2000 can also be incorporated into a hat, such as the baseball cap 2030 shown in FIGS. 57A, 57B. The engine 2000 can be incorporated into the hat band 2032 of the cap with the ends of the bungee cord 2002 projecting out from the brim to be engaged by clamps 2012, as depicted in FIG. 54A. As shown in FIG. 57B, the electrical wires 2006 may extend from the brim 2032 for attachment to a controller 2038 that can be mounted to the cap 2030. The compression engine can be configured as in the alternative embodiments described above in which the elastic element and SMA wires are co-extensive or in which the combined lengths of the components connected end-to-end encircle the hat. The controller 2038 can be configured like the controllers described herein to implement a compression protocol adapted to the head of the wearer. The controller can include output wiring that can be coupled to a power supply or external data source, or the power supply can be integrated into the controller. It can be appreciated that a similar controller can be incorporated into the trousers 2020 of FIGS. 56A, 56B. It should be appreciated that the articles of clothing in these embodiments are primarily intended for therapeutic measures. Thus, the embodiments depicted in these figures are not necessarily flattering to the wearer. However, it is contemplated that the compression engine 2002 and associated controller 2038 can be configured in a small and efficient package that can allow the wearer to wear the clothing while performing other activities.

Figure 58:
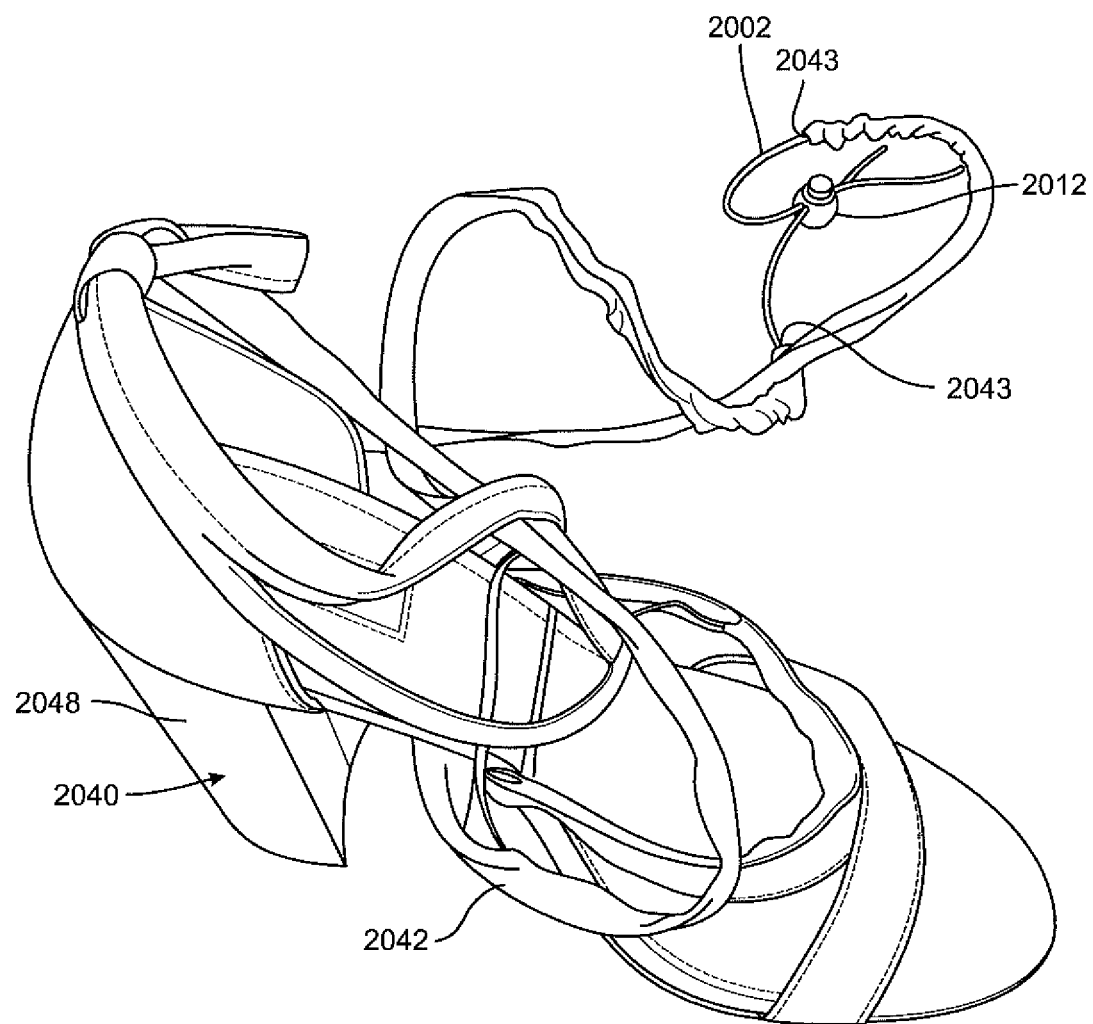
FIG. 58 is a perspective view of a dress shoe or high heel shoe incorporating the compression engine of FIGS. 52-53.

In another embodiment, the compression engine is incorporated into footwear, such as the dress shoe 2040 shown in FIG. 58. The compression engine 2000 is incorporated into the straps 2042 of the shoe, in which the straps are wound or ties around the foot and/or ankle of the wearer. The compression engine includes the elastic element or bungee cord 2002 extending from the free ends 2043 of the strap(s). Rather than tying the strap, the bungee cord provides the pre-tensioning necessary to hold the shoe on the wearer's foot. The free ends of the bungee cord 2002 can be connected with a single clamp 2012, as depicted in FIG. 54B. The electrical wires can also be integrated into the straps 2042 and fed to a controller mounted in the heel 2048 of the shoe. The controller can be implemented to maintain a desired tension in the compression engine, and therefore a desired compression or pressure on the foot of the wearer. The controller can thus operate interactively, as discussed in the previous embodiments, to maintain the desired pressure for all activities of the wearer.

Figure 59:
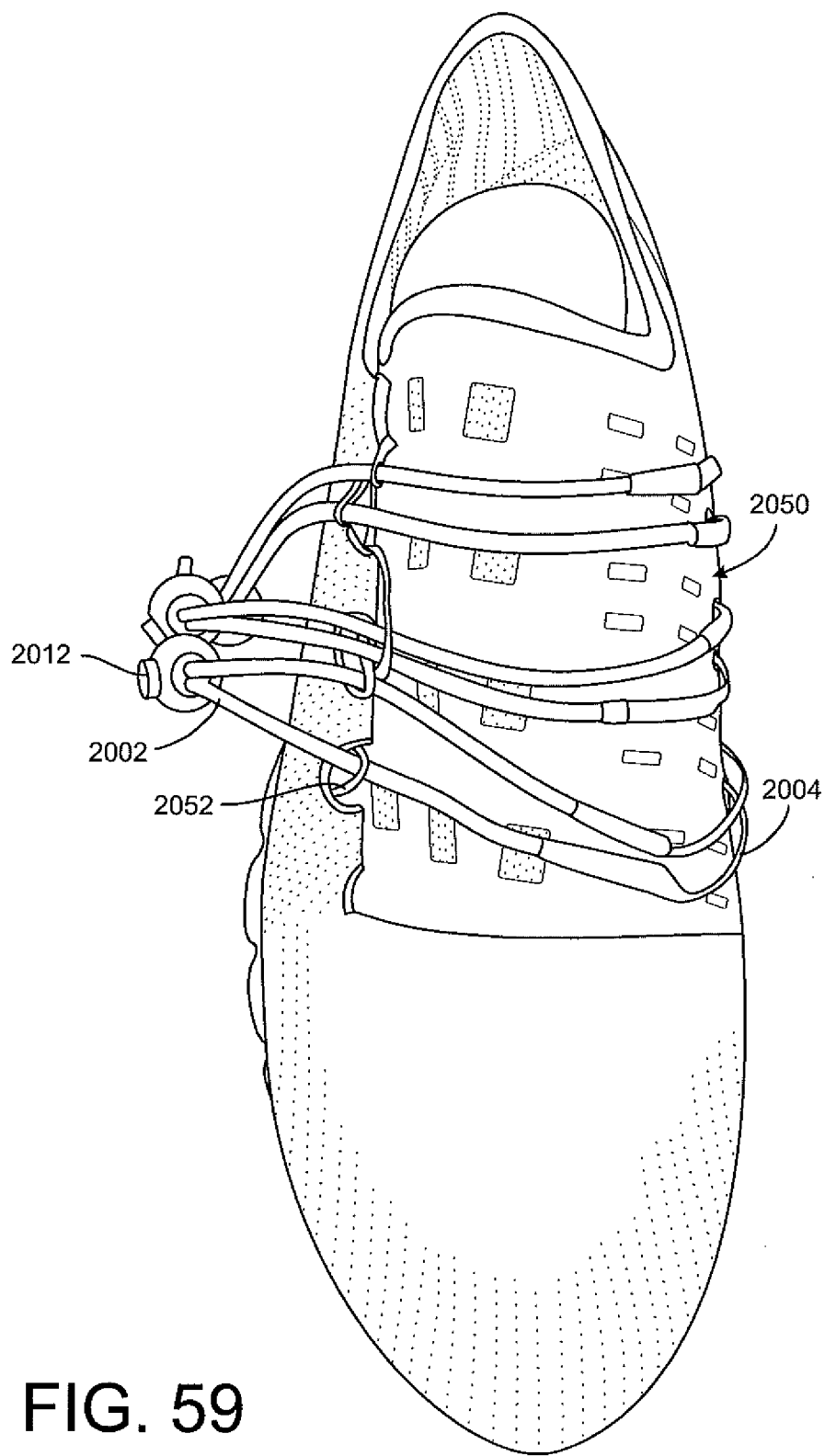
FIG. 59 is top view of an athletic shoe incorporating the compression engine of FIGS. 52-53.

A similar approach can be implemented in an athletic shoe, such as the shoe 2050 shown in FIG. 59. In this embodiment, a plurality of pre-tensioning elements or bungee cords can extend through eyelets 2052 of the shoe, with clamps 2012 used to fix the bungee cords to the shoe and to adjust the pre-tension in the compression engine. The SMA wires 2004 can be anchored to the shoe at the side of the shoe opposite the eyelets 2052 and extend across the top of the shoe, so that upon actuation of the SMA wires 2004 the compression engine compresses the upper portion of the shoe on the foot of the wearer. Alternatively, the SMA wires can encircle the foot, passing through the upper of the shoe and beneath the insole in a manner similar to the embodiment of FIGS. 45A-B, 46A-D. The compression protocol for this embodiment of the athletic shoe can be similar to the protocol administered for the shoe shown in FIGS. 46C-46D. The compression engine can encircle the foot to apply compression to the entire foot, or can alternatively extend across the top of the shoe to apply compression only at the top of the foot.

Figure 60:
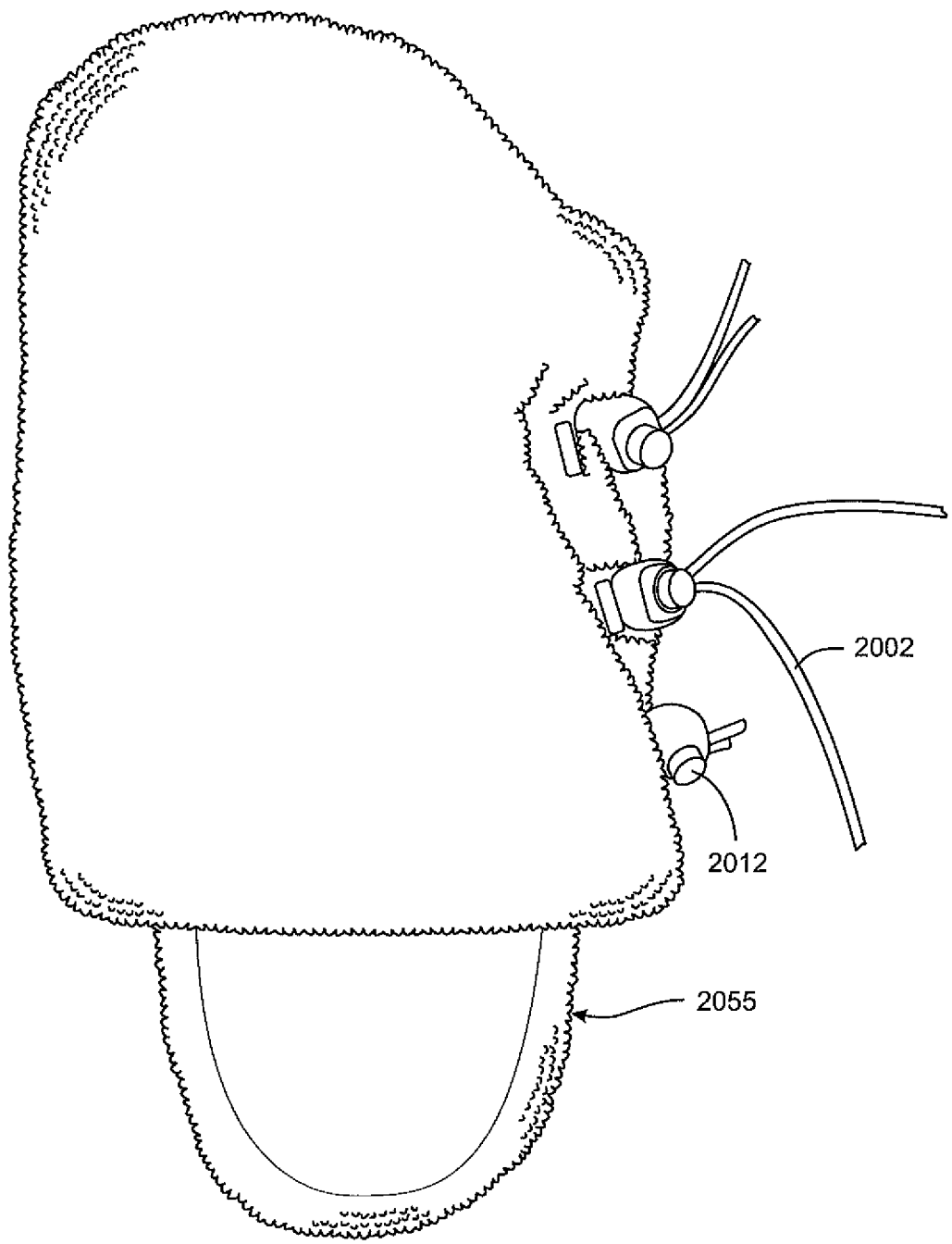
FIG. 60 is a top view of a slipper incorporating the compression engine of FIGS. 52-53.
Figure 61:
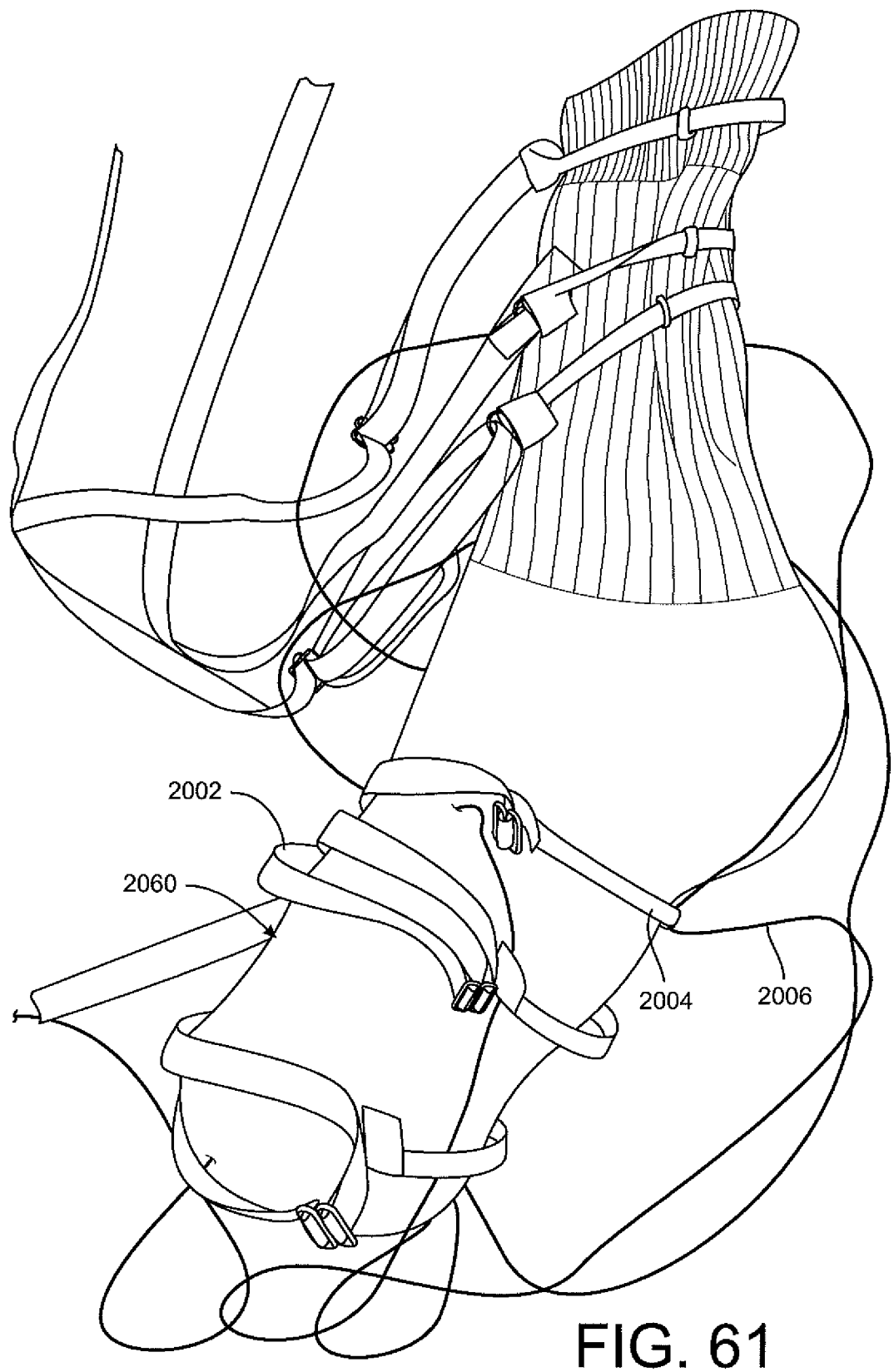
FIG. 61 is a side view of a sock incorporating the compression engine of FIGS. 52-53.

A similar approach can be implemented in the slipper 2055 shown in FIG. 60. The compression engine can extend through the upper portion of the slipper with the ends of the bungee cord 2002 adjustably tightened by the clamps 2012. The compression engine disclosed above can also be incorporated into the fabric of a sock 2060, as shown in FIG. 61. The bungee cords 2002 of the engine can extend across the top of the sock while the SMA wires 2004, appropriately protected by a shroud, can extend along the side and bottom of the sock. The wires 2006 can also be integrated into the sock for electrical connection to a controller, such as the controller 2038.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A device comprising:
a compression device for applying controllable compression to a portion of the anatomy of a user integrated into the device, the compression device including;
a plurality of shape memory wires integrated into the device to apply compression to a portion of the wearer's body wearing the device upon actuation of the plurality of wires;
a pre-tensioning apparatus including an elastic element connected to each of the plurality of shape memory wires and integrated into the device such that the elastic element substantially encircles the portion of the anatomy, and such that the pre-tensioning apparatus applies an initial tension to the plurality of shape-memory wires; and
a controller configured to selectively actuate one or more of the plurality of shape-memory wires to reduce the effective length of the wires, to thereby apply pressure to the portion of the wearer's body through the shape memory wires and the elastic element for the associated shape memory wire.

2. The device of claim 1, wherein:
the compression device is provided with an electrical power supply; and
the controller is configured to selectively apply a current from the power supply to one or more of the plurality of shape-memory wires.

3. The device of claim 1, wherein the elastic element is a bungee cord.

4. The device of claim 1, wherein:
the elastic element is integrated into the device with opposite ends of the elastic element extending outside the device; and the elastic element includes at least one adjustable clamp engaging each of the opposite ends of the elastic element to permit adjustment of the initial tension in the elastic element.

5. The device of claim 1, wherein:
the elastic element connected to a corresponding one of the plurality of shape memory wires is substantially co-extensive with the corresponding shape memory wire;
the length of the co-extensive elastic element and corresponding shape memory wire is sized to encircle the portion of the anatomy; and
the elastic element is connected to the corresponding shape memory wire at two locations in a middle portion of the elastic element.

6. The device of claim 5, wherein the elastic element is connected to the shape memory wire at the two locations by a fisherman's knot.

7. The device of claim 1, wherein each elastic element connected to a corresponding one of the plurality of shape memory wires includes a first elastic element connected end-to-end with one end of the corresponding shape memory wire and a second elastic element connected end-to-end with an opposite end of the corresponding shape memory wire, so that the combined length of the first and second elastic elements and the corresponding shape memory wire is sized to encircle the portion of the anatomy.

8. The device of claim 1, wherein the device is an article of clothing and the compression device is integrated into the article of clothing.

9. The device of claim 8, wherein the article of clothing is a trousers and the compression device is integrated into the trousers in the thigh region.

10. The device of claim 9, wherein the compression device is further integrated into the trousers in the lower leg region.

11. The device of claim 8, wherein the article of clothing is a hat and the compression device is integrated into the hat band of the hat.

12. The device of claim 8, wherein the article of clothing is a formal shoe having a strap arrangement for encircling the foot and/or ankle of the wearer, wherein the compression device is integrated into the strap arrangement.

13. The device of claim 8, wherein the article of clothing is an article of footwear and the compression device extends across the upper portion of the footwear.

14. The device of claim 13, wherein the compression device is anchored to the footwear at one side of the footwear, extends across the upper portion of the footwear and includes at least one clamp clamping the compression device at the opposite side of the footwear.

15. The device of claim 13, wherein the footwear is an athletic shoe or a slipper.

16. The device of claim 8, wherein the article of clothing is a sock and the compression device is integrated into the sock to encircle the sock.

17. The device of claim 1, wherein the elastic element includes a marker that is hidden within the device in a free state of the elastic element, and that is exposed outside the device when the elastic element is stretched a pre-determined amount.

18. The device of claim 1, wherein the pre-tensioning element includes a fastening strip attached to a free end of the elastic element outside the device, the fastening strip adapted to be fastened to the device when the device is worn on the wearer's body.

* * * * *